US012676239B2

(12) United States Patent
Cistola et al.

(10) Patent No.: US 12,676,239 B2
(45) Date of Patent: Jul. 7, 2026

(54) METHODS AND TOOLS FOR PREDICTING CARDIOMETABOLIC HEALTH BY COMBINING BLOOD T2 PARAMETERS WITH OTHER MEASURES

(71) Applicant: Texas Tech University System, Lubbock, TX (US)

(72) Inventors: David P. Cistola, El Paso, TX (US); Alok K. Dwivedi, El Paso, TX (US); Erin B. Campbell, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 18/886,100

(22) Filed: Sep. 16, 2024

(65) Prior Publication Data

US 2026/0081028 A1 Mar. 19, 2026

(51) Int. Cl.
| | |
|---|---|
| *G16H 50/30* | (2018.01) |
| *G16H 10/40* | (2018.01) |
| *G16H 10/60* | (2018.01) |
| *G16H 20/10* | (2018.01) |
| *G16H 50/20* | (2018.01) |

(52) U.S. Cl.
CPC ............. *G16H 50/30* (2018.01); *G16H 10/40* (2018.01); *G16H 10/60* (2018.01); *G16H 20/10* (2018.01); *G16H 50/20* (2018.01)

(58) Field of Classification Search
None
See application file for complete search history.

(56) References Cited

U.S. PATENT DOCUMENTS

| | | |
|---|---|---|
| 7,715,901 B2 | 5/2010 | Salomon et al. |
| 2004/0057940 A1 | 3/2004 | Kim et al. |

(Continued)

FOREIGN PATENT DOCUMENTS

| | | |
|---|---|---|
| EP | 3 253 287 B1 | 3/2021 |
| WO | WO 2016/176668 | 11/2016 |
| WO | WO 2024/097429 | 5/2024 |

OTHER PUBLICATIONS

Robinson, Michelle D., et al. "Water T 2 as an early, global and practical biomarker for metabolic syndrome: an observational cross-sectional study." Journal of translational medicine 15 (2017): 1-19. (Year: 2017).*

(Continued)

*Primary Examiner* — Karlheinz R. Skowronek
*Assistant Examiner* — Mary C Leverett
(74) *Attorney, Agent, or Firm* — Farhang Amini; Shackelford, McKinley & Norton, LLP

(57) ABSTRACT

Embodiments pertain to a method of assessing the cardio-metabolic health of a subject by (1) receiving a plurality of parameters of the subject, where the plurality of parameters includes a $T_2$ relaxation time constant of a subject's blood ($T_2$ value) and one or more additional parameters; and (2) feeding the plurality of parameters into an algorithm, where the algorithm correlates the plurality of parameters to the subject's cardiometabolic health. The methods may also include a step of communicating cardiometabolic health risk. The methods may also include a step of implementing a treatment decision. Further embodiments pertain to system for assessing the cardiometabolic health of a subject in accordance with such methods.

20 Claims, 40 Drawing Sheets

(56) References Cited

U.S. PATENT DOCUMENTS

| | | | |
|---|---|---|---|
| 2006/0011199 A1 | 1/2006 | Rashad et al. | |
| 2011/0059475 A1 | 3/2011 | May et al. | |
| 2017/0224259 A1 | 8/2017 | Simonetti et al. | |
| 2018/0020947 A1 | 1/2018 | Cistola et al. | |
| 2018/0113141 A1 | 4/2018 | Lowery, Jr. et al. | |
| 2019/0247010 A1 | 8/2019 | Barnacka | |
| 2020/0383574 A1 | 12/2020 | Cima et al. | |
| 2022/0039680 A1* | 2/2022 | Cistola | A61B 5/14532 |
| 2022/0142530 A1 | 5/2022 | Lim et al. | |
| 2023/0056088 A1 | 2/2023 | Crawley et al. | |
| 2024/0310465 A1 | 9/2024 | Cistola et al. | |

OTHER PUBLICATIONS

Collewet, Guylaine, et al. "Multi-exponential Mri T2 maps: A tool to classify and characterize fruit tissues." Magnetic Resonance Imaging 87 (2022): 119-132. (Year: 2022).*

Cistola, David P., and Michelle D. Robinson. "Compact NMR relaxometry of human blood and blood components." TrAC Trends in Analytical Chemistry 83 (2016): 53-64. (Year: 2016).*

Croft, Jacob, et al. "Plasma water T2 detects age-stratified differences in cardiometabolic health among familial CCM patients with Hispanic CCM1 mutation." Metabolic Brain Disease (2024): 1-9. (Year: 2024).*

Office Action for U.S. Pat. App. No. 18/608, 144, mailed on Aug. 5, 2024.

Chien et al., MR Gradient Echo Imaging of Intravascular Blood Oxygenation: T2* Determination in the Presence of Flow; Aug. 1994; Magnetic resonance in medicine; 32.4; pp. 540-545.

Cosinuss et al., "Oxygen Saturation"; webpage <https://www.cosinuss.com/en/measured-data/vital-signs/oxygen-saturation/>; 1 page; Apr. 11, 2021.

Choi et al. Effects of chemical modification of wheat starch on molecular mobility as studied by pulsed 1H NMR; Pub. Date Oct. 2, 2002; LWT-Food Science and Technology; vol. 36.1; pp. 105-112.

Cleveland et al., "Blood Oxygen Level"; webpage <https://my.clevelandclinic.org/health/diagnostics/22447-blood-oxygen-level>; 14 pages; Apr. 19, 2022.

International Search Report for PCT/US2024/020371, mailed on Jul. 1, 2024.

International Search Report for PCT/US2025/046543, mailed on Feb. 2, 2026.

* cited by examiner

LEGEND

| | | |
|---|---|---|
| 0.00 TO 0.49 UNACCEPTABLE | 0.60 TO 0.69 MEDIOCRE | 0.80 TO 0.89 MERITORIOUS |
| 0.50 TO 0.59 MISERABLE | 0.70 TO 0.79 MIDDLING | 0.90 TO 1.00 MARVELOUS |

LEGEND
| | | |
|---|---|---|
| ▨ 0.00 TO 0.49 UNACCEPTABLE | ▨ 0.60 TO 0.69 MEDIOCRE | ▨ 0.80 TO 0.89 MERITORIOUS |
| ▨ 0.50 TO 0.59 MISERABLE | ▨ 0.70 TO 0.79 MIDDLING | ▨ 0.90 TO 1.00 MARVELOUS |

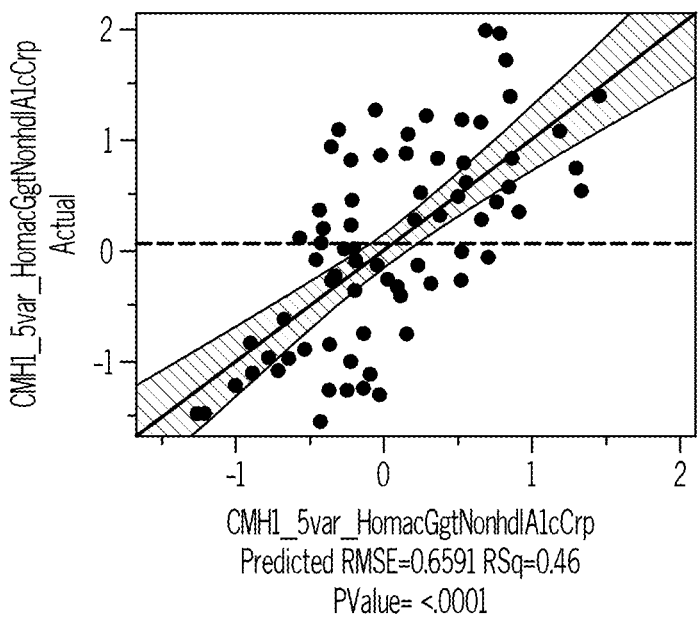
CMH1_5var_HomacGgtNonhdlA1cCrp
Predicted RMSE=0.6591 RSq=0.46
PValue= <.0001
FIG. 4A
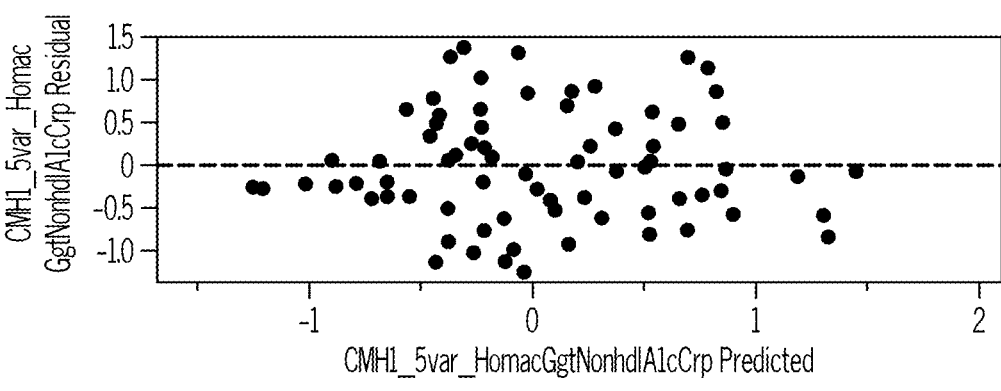
CMH1_5var_HomacGgtNonhdlA1cCrp Predicted
FIG. 4B
FIG. 4C

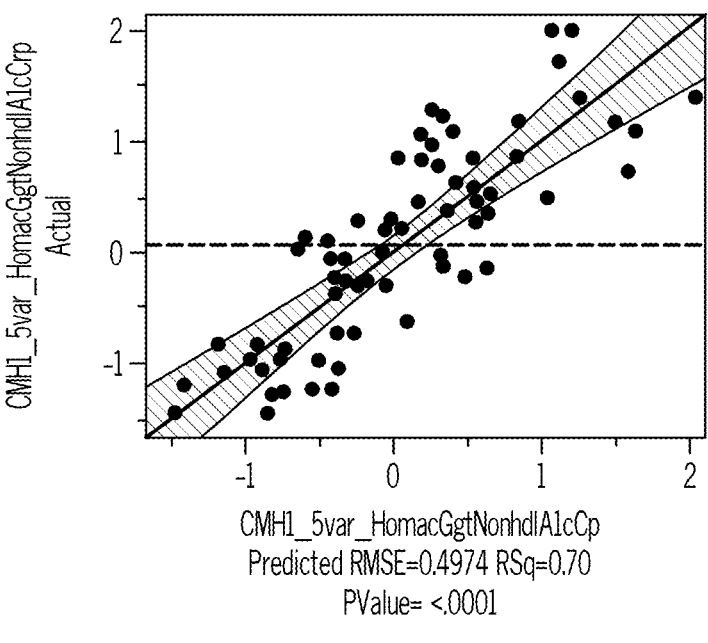
FIG. 5A
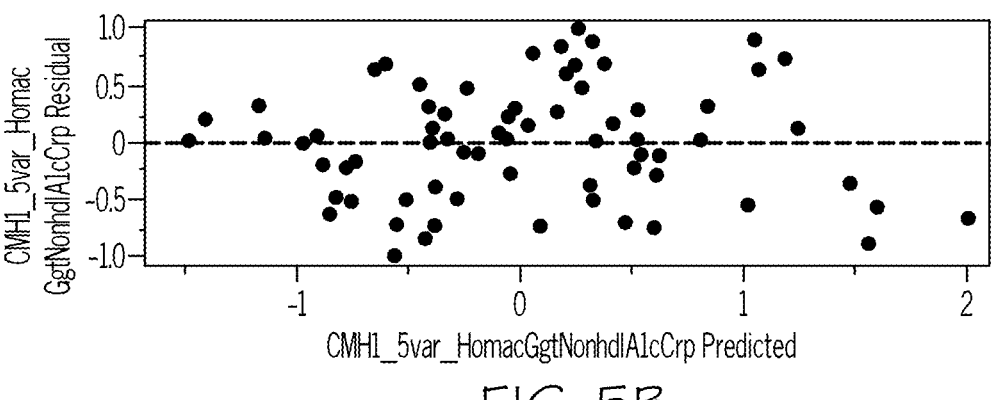
FIG. 5B
FIG. 5C

CMH1_5var_HomacGgtNonhdlA1cCrp
Predicted RMSE=0.7668 RSq=0.27
PValue= <.0001

CMH1_5var_HomacGgtNonhdlA1cCrp
Predicted RMSE=0.5664 RSq=0.61
PValue= <.0001

CMH14_HomacGgtFibNonhdlLac Predicted
RMSE=0.5657 RSq=0.64 PValue=<.0001

CMH14_HomacGgtFibNonhdlLac Predicted

Row Number

CMH 14_HomacGgtFibNonhdlLac Predicted
RMSE=0.421 RSq=0.81 PValue=<.0001

CMH14_HomacGgtFibNonhdlLac Predicted

Row Number

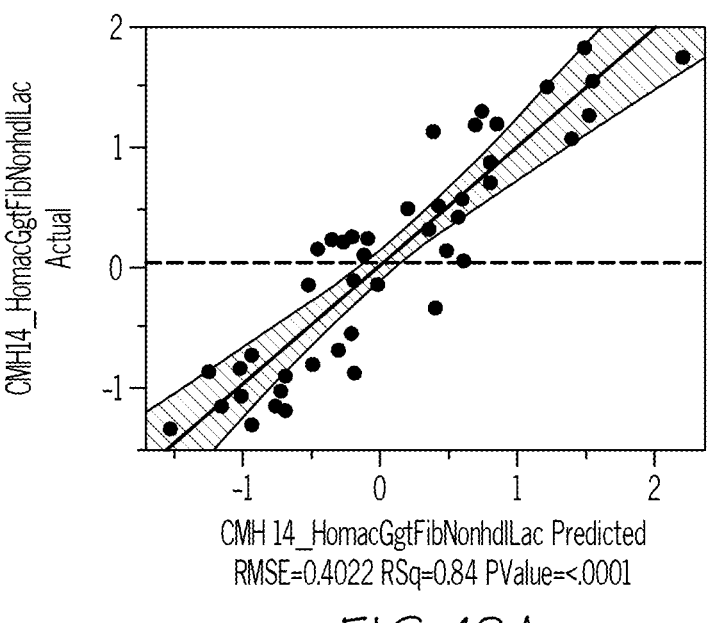
CMH 14_HomacGgtFibNonhdlLac Predicted
RMSE=0.4022 RSq=0.84 PValue=<.0001
FIG. 12A
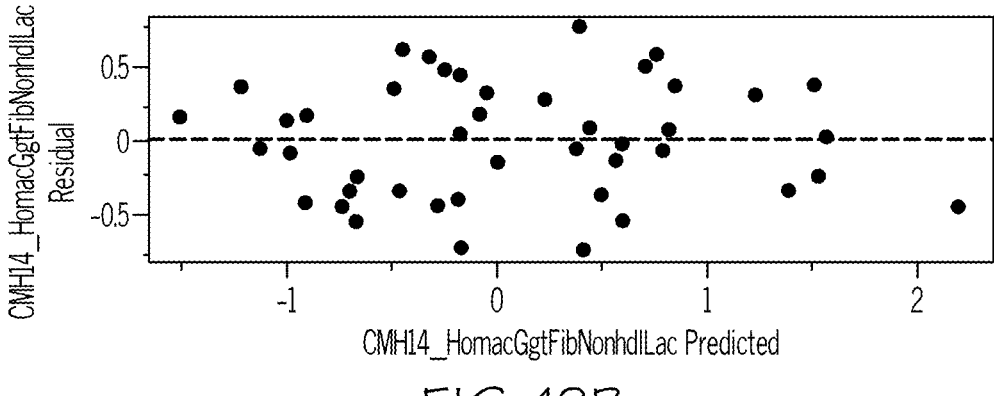
CMH14_HomacGgtFibNonhdlLac Predicted
FIG. 12B
FIG. 12C RMSE=0.472 RSq=0.77 PValue=<.0001

METHODS AND TOOLS FOR PREDICTING CARDIOMETABOLIC HEALTH BY COMBINING BLOOD T2 PARAMETERS WITH OTHER MEASURES

BACKGROUND

A need exists for more sensitive and readily accessible screening tools for assessing cardiometabolic health, especially in asymptomatic individuals with hidden risk factors for early screening, ease of shared-decision making, disease management, implementing treatments, and disease control. Numerous embodiments of the present disclosure aim to address the aforementioned need.

SUMMARY

In some embodiments, the present disclosure pertains to a method of assessing the cardiometabolic health of a subject. In some embodiments, the methods of the present disclosure include: (1) receiving a plurality of parameters of the subject, where the plurality of parameters includes a $T_2$ relaxation time constant of a subject's blood ($T_2$ value), and one or more additional parameters; and (2) feeding the plurality of parameters into an algorithm, where the algorithm correlates the plurality of parameters to the subject's cardiometabolic health. In some embodiments, the methods of the present disclosure also include a step of communicating cardiometabolic health risk. In some embodiments, the methods of the present disclosure also include a step of implementing a treatment decision. In some embodiments, the method is repeated after implementing the treatment decision, such as for disease progression, control and further management.

Additional embodiments of the present disclosure pertain to a system for assessing the cardiometabolic health of a subject. In some embodiments, the system includes one or more computer-readable storage mediums having a program code embodied therewith. In some embodiments, the program code includes programming instructions for:

(1) receiving a plurality of parameters of the subject, where the plurality of parameters include a $T_2$ relaxation time constant of a subject's blood ($T_2$ value) and one or more additional parameters;

and (2) feeding the plurality of parameters into an algorithm, where the algorithm correlates the plurality of parameters to the subject's cardiometabolic health. In some embodiments, the systems of the present disclosure also include programming instructions for communicating cardiometabolic health risk. In some embodiments, the systems of the present disclosure also include programming instructions for recommending a treatment decision.

DESCRIPTION OF THE DRAWINGS

FIGS. 4A-4F provide multi-variable linear regression statistical reports for MR1A, including an actual by predicted plot (FIG. 4A), a residual by predicted plot (FIG. 4B), a studentized residuals plot (FIG. 4C), a residual by row plot (FIG. 4D), a residual normal quantile plot (FIG. 4E), and a prediction profiler (FIG. 4F).

FIGS. 5A-5F provide multi-variable linear regression statistical reports for MR1B, including an actual by predicted plot (FIG. 5A), a residual by predicted plot (FIG. 5B), a studentized residuals plot (FIG. 5C), a residual by row plot (FIG. 5D), a residual normal quantile plot (FIG. 5E), and a prediction profiler (FIG. 5F).

FIGS. 12A-12F provide multi-variable linear regression statistical reports for MR3C, including an actual by predicted plot (FIG. 12A), a residual by predicted plot (FIG. 12B), a studentized residuals plot (FIG. 12C), a residual by row plot (FIG. 12D), a residual normal quantile plot (FIG. 12E), and a prediction profiler (FIG. 12F).

DETAILED DESCRIPTION

Figure 1A:
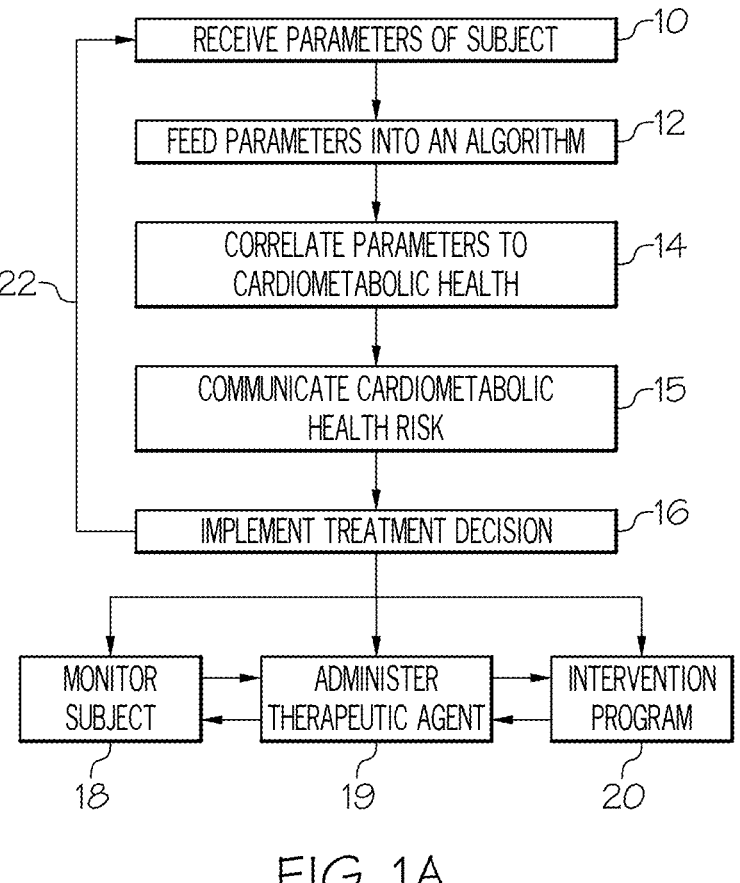
FIG. 1A illustrates a method of assessing the cardiometabolic health of a subject.

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials define a term in a manner that contradicts the definition of that term in this application, this application controls.

Poor cardiometabolic health (CMH) is a risk factor for common chronic diseases, including type 2 diabetes, cardiovascular disease, dementia and some forms of cancer. In addition, poor CMH increases susceptibility to severe outcomes from infectious diseases, such as COVID-19 and influenza. Moreover, the metabolic imbalance can impede human performance for numerous individuals, such as athletes, pilots, warfighters, first responders and other active individuals.

A conventional medical examination (i.e., a wellness examination from a healthcare provider) includes a history and physical exam with routine blood testing. The latter often includes a complete blood count (CBC), a comprehensive metabolic panel (CMP), and a lipid panel. Together, these panels include 30-40 individual diagnostic tests designed to assess specific aspects of an individual's health status. A wellness exam can unveil some undiagnosed conditions, such as prediabetes, metabolic syndrome or overt diabetes. However, conventional medical examinations are unable to fully assess the cardiometabolic health of asymptomatic individuals. For instance, conventional medical examinations do not detect hidden risk factors ("residual risk") that can damage the insulin-secreting beta cells of the pancreas, leading to diabetes, and the internal walls of arteries, leading to atherosclerosis.

Thus, there is an unmet need for practical screening tools to identify asymptomatic individuals with less-than-optimal cardiometabolic health. Ideally, this screening should occur in apparently healthy teens and young adults, before significant cell or tissue damage occurs.

In fact, nearly half of the United States population has some degree of poor metabolic health. For instance, approximately 10% of the United States population (i.e., 30 million people) have an early metabolic imbalance (EMI), a hidden risk factor for diabetes and atherosclerotic cardiovascular disease (ASCVD) that goes undetected during a conventional medical examination.

Accordingly, a need exists for more sensitive and readily accessible screening tools for detecting cardiometabolic health (e.g., poor or less-than-optimal cardiometabolic health). Numerous embodiments of the present disclosure aim to address the aforementioned need.

In some embodiments, the present disclosure pertains to a method of assessing cardiometabolic health of a subject. In some embodiments illustrated in FIG. 1A, the methods of the present disclosure include: receiving a plurality of parameters of the subject, where the plurality of parameters includes a $T_2$ relaxation time constant of a subject's blood ($T_2$ value) and one or more additional parameters (step 10); and feeding the plurality of parameters into an algorithm (step 12), where the algorithm correlates the plurality of parameters to the subject's cardiometabolic health (step 14).

In some embodiments, the methods of the present disclosure also include a step of communicating cardiometabolic health risk (step 15). In some embodiments, the methods of the present disclosure also include a step of implementing a treatment decision (step 16). In some embodiments, the treatment decision includes monitoring the subject for signs or symptoms of one or more cardiometabolic health-related conditions (step 18), administering a therapeutic agent to the subject (step 19), and/or administering an intervention program for the subject (step 20). In some embodiments, the method is repeated after implementing the treatment decision (step 22).

Additional embodiments of the present disclosure pertain to a system for assessing cardiometabolic health of a subject. In some embodiments, the system includes one or more computer-readable storage mediums having a program code embodied therewith. In some embodiments, the program code includes programming instructions for:

(1) receiving a plurality of parameters of the subject, where the plurality of parameters include a $T_2$ relaxation time constant of a subject's blood ($T_2$ value) and one or more additional parameters;

and (2) feeding the plurality of parameters into an algorithm, where the algorithm correlates the plurality of parameters to the subject's cardiometabolic health.

In some embodiments, the systems of the present disclosure also include programming instructions for communicating cardiometabolic health risk. In some embodiments, the systems of the present disclosure also include programming instructions for recommending a treatment decision.

As set forth in more detail herein, the methods and systems of the present disclosure can have numerous embodiments.

$T_2$ Values:

The methods and systems of the present disclosure may receive various $T_2$ values of a subject's blood. For instance, in some embodiments, the $T_2$ value represents the spin-spin relaxation time constant of the plasma or serum water component of the blood sample after removing the blood cells or any blood clots, respectively. In some embodiments, the $T_2$ value represents the spin-spin relaxation time constant of the isolated plasma component of the blood sample (plasma water $T_2$). In some embodiments, the $T_2$ value represents the spin-spin relaxation time constant of the isolated serum component of the blood sample (serum water $T_2$).

In some embodiments, the $T_2$ value represents the spin-spin relaxation time constant of the settled blood cell pellet component of an anti-coagulated whole blood sample ($T_{2P}$). In some embodiments, the blood cell pellet component includes whole blood cells. In some embodiments, the blood cell pellet component includes isolated blood cells. In some embodiments, the isolated blood cells include red blood cells.

In some embodiments, the $T_2$ value represents the spin-spin relaxation time constant of the supernatant liquid component of an anti-coagulated whole blood sample ($T_{2S}$). In some embodiments, the sample is in the form of a mixed, unsettled whole blood sample (whole blood $T_2$). In some embodiments, the blood cell component is in the form of a whole blood sample. In some embodiments, the blood cell component is in the form of a pellet or supernatant of an anti-coagulated whole blood sample. In some embodiments, the liquid component is separated from the cells or clot and analyzed separately (plasma water $T_2$ or serum water $T_2$). In some embodiments, the blood cell component is separated from the liquid plasma and analyzed separately (blood cell $T_2$ or red blood cell $T_2$).

In some embodiments, the $T_2$ value is represented in the following multi-exponential formula:

$$I(t) = \sum_i A_i e^{-t/T_{2i}}$$

In some embodiments, I(t) represents the nuclear magnetic resonance (NMR) signal intensity, $A_i$ represents the signal amplitude, and $T_2$; represents the transverse relaxation time constant of ith proton microenvironment or mobility domain. In some embodiments, when i=P, the proton microenvironment being measured is the blood cell pellet in an anti-coagulated, sedimented whole blood sample (whole blood $T_{2P}$). As red blood cells outnumber white blood cells and platelets by ~1000:1, the dominant contributor to $T_{2P}$ is the water inside red blood cells. In some embodiments, the value of $T_{2P}$ is influenced by water interactions with hemoglobin, as $T_{2P}$ probes variations in the concentration, oxygenation and oxidation states of hemoglobin. In some embodiments, the $T_{2P}$ term is resolved from other terms using a suitable multi-exponential fitting algorithm, such as a discrete components analysis algorithm utilizing singular value decomposition, an inverse Laplace transformation, a matrix pencil method, or any other suitable multi-exponential analysis algorithm. In some embodiments, when i=S, the proton microenvironment being measured is the liquid supernatant on top of the blood cell pellet. The dominant contributors to $T_{2S}$ are the water molecules in plasma, which bind and exchange on and off plasma proteins and lipoproteins, sensing changes in those proteins resulting from changes in metabolism. In some embodiments, whole blood $T_{2S}$ is also influenced by a magnetic susceptibility gradient arising from the paramagnetic blood cell pellet.

$T_2$ values in blood samples may be measured in various manners. For instance, in some embodiments, $T_2$ values may be measured through the utilization of a magnetic resonance device, a magnetic resonance relaxometry device, a tabletop magnetic resonance device, a miniaturized magnetic resonance device, a benchtop magnetic resonance device, a time-domain magnetic resonance device, a magnetic resonance spectroscopy device, a magnetic resonance imaging device, a nuclear magnetic resonance device, or combinations thereof.

Additional Parameters

The methods and systems of the present disclosure may also receive various additional parameters. For instance, in some embodiments, the one or more additional parameters include, without limitation, body-mass index, age, resting pulse rate, serum uric acid levels, serum uric acid/creatinine ratio, dynamic light scattering diffusion times of the subject's blood, dynamic light scattering diffusion intensities of the subject's blood, a nutritional risk index of the subject, social determinants of health, behavioral determinants of health, lifestyle-related measurements, or combinations thereof.

In some embodiments, more than one $T_2$ value may be combined with additional parameters. For instance, in some embodiments, both plasma water $T_2$ and whole blood $T_{2P}$ may be combined with body-mass index, age, and resting pulse rate. In some embodiments, such parameters may be combined in a regression algorithm that predicts cardiometabolic health.

In some embodiments, the plurality of parameters includes a $T_2$ value, age, body-mass index, and resting pulse rate. In some embodiments, the plurality of parameters includes plasma or serum water $T_2$, age, body-mass index, and resting pulse rate. In some embodiments, the plurality of parameters includes a $T_2$ value and a serum uric acid/creatinine ratio. In some embodiments, the plurality of parameters includes plasma or serum water $T_2$, body-mass index, age and serum uric acid/creatinine ratio. In some embodiments, the plurality of parameters includes $T_2$ value and at least one of dynamic light scattering diffusion intensities of the subject's blood and/or dynamic light scattering diffusion times of the subject's blood. Table 1 provides additional combinations of parameters.

The parameters of the present disclosure may be obtained from various sources. For instance, in some embodiments, one or more of the parameters may be obtained from a blood sample of a subject. In some embodiments, $T_2$ values may be obtained from a blood sample of a subject.

The parameters of the present disclosure may be obtained from various blood samples. For instance, in some embodiments, the blood sample includes a whole blood sample. In some embodiments, the whole blood sample contains an anti-coagulant to prevent the blood from clotting. In some embodiments, the blood sample includes a plasma or serum component of a blood sample. For instance, in some embodiments, a liquid component of the blood sample is separated from the blood cells or clot to form plasma or serum.

In some embodiments, the blood sample includes a blood cell component of the blood sample. In some embodiments, the blood cell component includes red blood cells, white blood cells, and platelets. In some embodiments, the blood cell component is mostly composed of red blood cells, but also white blood cells and platelets.

In some embodiments, the blood cell component is in the form of a pellet that settles to the bottom of the sample tube. In some embodiments, the pelleted blood cell component is settled or separated from the liquid plasma (i.e., the non-cellular liquid component of the blood) in an anti-coagulated sample of whole blood. In some embodiments, the pelleted blood cell component is in the form of a separated pellet formed by centrifuging the sample, or by spontaneous settling of the cells to the bottom of the tube. In some embodiments, such a process separates the cells from the supernatant plasma. In some embodiments, the settled or separated blood cell component of the blood sample is in an anti-coagulated form.

In some embodiments, the blood cell component is in the form of a pellet of an anti-coagulated whole blood sample. In some embodiments, the blood cell pellet represents a settled and anti-coagulated whole blood sample.

In some embodiments, the blood cell component is purified and isolated from the plasma. In some embodiments, the red blood cell component is purified and isolated from the white blood cell, platelet and plasma components. In some embodiments, the blood sample includes a pelleted blood cell component that is settled or separated from the liquid plasma in an anti-coagulated sample of whole blood.

In some embodiments, the methods of the present disclosure also include a step of obtaining a blood sample from a subject. For instance, in some embodiments, a blood sample is obtained from a subject through venipuncture. In some embodiments, a blood sample is obtained from a subject through a fingerstick drop or an upper arm blood collection device equipped with a microtainer tube.

Algorithms

The methods and systems of the present disclosure can utilize various algorithms. In some embodiments, the systems of the present disclosure also include the algorithm. In some embodiments, the algorithms may be operable for multi-exponential analysis of the $T_2$ decay curve. In some embodiments, the algorithm includes a discrete components analysis module utilizing singular value decomposition. In some embodiments, the algorithm includes an inverse Laplace transform algorithm. In some embodiments, the algorithm includes a matrix pencil algorithm for multi-exponential analysis.

In some embodiments, the algorithm includes a multi-variable linear regression algorithm, a logistic regression algorithm, a machine-learning algorithm, or an artificial intelligence algorithm trained on the plurality of parameters. In some embodiments, the algorithm includes a regression algorithm for predicting cardiometabolic health. In some embodiments, the regression algorithm includes a multi-variable linear or logistic regression algorithm. In some embodiments, the algorithm includes a machine-learning or artificial intelligence algorithm trained on the plurality of parameters. In some embodiments, the training of the machine learning or artificial intelligence algorithm is conducted using a random forest or bootstrap forest procedure to assess the correlation between the plurality of parameters and cardiometabolic health and to predict the subject's cardiometabolic health.

In some embodiments, factor analysis, variable cluster or latent profile or class models may be used to determine the different homogenous grouping of cardiometabolic health predicted by $T_2$. In some embodiments, the models may be developed and validated using K-class cross-validation methods.

In some embodiments, the machine learning or artificial intelligence algorithm is an L1-regularized logistic regression algorithm. In some embodiments, the machine learning or artificial intelligence algorithm includes supervised learning algorithms. In some embodiments, the supervised learning algorithms include nearest neighbor algorithms, naïve-Bayes algorithms, decision or regression tree algorithms, linear regression algorithms, support vector machines, neural networks, convolutional neural networks, ensembles (e.g., random forests and gradient-boosted decision trees), generalized additive models, multifactorial polynomial regression models, or combinations of regression methods (e.g., parametric, semiparametric, and/or nonparametric regression models). In some embodiments, the algorithms of the present disclosure include generalized additive models, multifactorial polynomial regression models, unsupervised or supervised machine learning models, dimension reduction methods, or quantile regressions to capture linear, nonlinear and heterogeneity in predictive performance.

Correlation of Parameters to Cardiometabolic Health

The algorithms of the present disclosure may be utilized to correlate parameters to a subject's cardiometabolic health in various manners. For instance, in some embodiments, the correlation includes a quantitative estimation of a subject's current cardiometabolic health status, diagnosis of a cardiometabolic health-related condition in a subject, prediction of a subject's susceptibility to a cardiometabolic health-related condition, or combinations thereof. In some embodiments, the correlation includes prediction of a subject's susceptibility to a cardiometabolic health-related condition.

The algorithms of the present disclosure may correlate parameters to various cardiometabolic health-related conditions. For instance, in some embodiments, the cardiometabolic health-related condition includes, without limitation, metabolic syndrome, early metabolic syndrome, metabolic dysregulation, early metabolic dysregulation, metabolic imbalance, early metabolic imbalance, diabetes, prediabetes, type 2 diabetes, gestational diabetes, insulin resistance, dyslipidemia, oxidative stress, subclinical inflammation, hypoxemia, subclinical hypoxemia, hypoxia, subclinical hypoxia, cardiovascular disease, endocrine disorders, hormonal disorders, kidney dysfunction, kidney failure, metabolism-associated fatty liver disease (MAFLD), steatohepatitis (MASH), cognition decline, dementia, or combinations thereof.

Communicating Cardiometabolic Health Risk

In some embodiments, the methods of the present disclosure also include a step of communicating cardiometabolic health risk. In some embodiments, the systems of the present disclosure also include programming instructions for communicating cardiometabolic health risk. In some embodiments, cardiometabolic health risk communication includes, without limitation, generation of risk scores (e.g., simplified predictive risk scores), generation of nomograms, or combinations thereof.

In some embodiments, cardiometabolic health risk communication occurs prior to a treatment decision. In some embodiments, cardiometabolic health risk communication may be utilized to facilitate a treatment decision. In some embodiments, cardiometabolic health risk communication may be utilized for shared decision-making processes.

In some embodiments, cardiometabolic health risk communication may be used to facilitate further assessments. For instance, in some embodiments, cardiometabolic health risk communication may be used to facilitate a further diagnostic work-up of a subject and/or monitoring a subject for related symptoms.

Cardiometabolic health risk communication may occur in various manners. For instance, in some embodiments, cardiometabolic health risk communication may occur through the utilization of a graphical user interface. In some embodiments, cardiometabolic health risk communication may occur through the utilization of a web-based integration tool.

Treatment Decision

In some embodiments, the methods of the present disclosure also include a step of implementing a treatment decision. In some embodiments, the systems of the present disclosure also include programming instructions for recommending a treatment decision. In some embodiments, the methods of the present disclosure may be repeated after implementing the treatment decision.

The methods and systems of the present disclosure may implement or recommend various treatment decisions. For instance, in some embodiments, the treatment decision includes monitoring the subject for signs or symptoms of one or more cardiometabolic health-related conditions, administering a therapeutic agent to the subject, administering an intervention program for the subject, or combinations thereof.

In some embodiments, the treatment decision includes administering an intervention program for the subject. In some embodiments, the intervention program includes, without limitation, a nutritional program, a physical activity program, a non-pharmaceutical intervention, or combinations thereof.

Subject

The methods and systems of the present disclosure may be utilized to assess cardiometabolic health in various subjects. For instance, in some embodiments, the subject is a human being. In some embodiments, the subject shows no visible signs or symptoms related to cardiometabolic health-related conditions. In some embodiments, the subject shows no visible signs or symptoms related to cardiometabolic health-related conditions but may have hidden risk factors. For instance, in some embodiments, the subject has undiagnosed early metabolic imbalance, prediabetes, metabolic syndrome, overt type 2 diabetes or ASCVD. In some embodiments, the subject has a diagnosed and documented metabolic condition but may utilize the methods and systems of the present disclosure to seek an estimate of the cardiometabolic severity of that condition.

Systems

The systems of the present disclosure may have various architectures and forms. For instance, in some embodiments, the systems of the present disclosure are in the form of a web-based program, an application-based program, or combinations thereof. In some embodiments, the systems of the present disclosure include an algorithm of the present disclosure, such as a machine-learning algorithm or artificial intelligence algorithm.

The systems of the present disclosure can include various types of computer-readable storage mediums. For instance, in some embodiments, the computer-readable storage medium can be a tangible device that can retain and store instructions for use by an instruction execution device. In some embodiments, the computer-readable storage medium may include, without limitation, an electronic storage device, a magnetic storage device, an optical storage device, an electromagnetic storage device, a semiconductor storage device, or combinations thereof. A non-exhaustive list of more specific examples of suitable computer-readable storage medium includes, without limitation, a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device, or combinations thereof.

A computer-readable storage medium, as used herein, is not to be construed as being transitory signals per se. Such transitory signals may be represented by radio waves or other freely propagating electromagnetic waves, electromagnetic waves propagating through a waveguide or other transmission media (e.g., light pulses passing through a fiber-optic cable), or electrical signals transmitted through a wire.

In some embodiments, computer-readable program instructions for systems can be downloaded to respective computing/processing devices from a computer-readable storage medium or to an external computer or external storage device via a network, such as the Internet, a local area network (LAN), a wide area network (WAN) and/or a wireless network. In some embodiments, the network may include copper transmission cables, optical transmission fibers, wireless transmission, routers, firewalls, switches, gateway computers and/or edge servers. In some embodiments, a network adapter card or network interface in each computing/processing device receives computer-readable program instructions from the network and forwards the computer-readable program instructions for storage in a computer-readable storage medium within the respective computing/processing device.

In some embodiments, computer-readable program instructions for carrying out operations of the present disclosure may be assembler instructions, instruction-set-architecture (ISA) instructions, machine instructions, machine-dependent instructions, microcode, firmware instructions, state-setting data, configuration data for integrated circuitry, or either source code or object code written in any combination of one or more programming languages, including an object-oriented programming language such as Smalltalk, C++, or the like, and procedural programming languages, such as the "C" programming language or similar programming languages.

In some embodiments, the computer-readable program instructions may execute entirely on the user's computer, partly on the user's computer, as a stand-alone software package, partly on the user's computer and partly on a remote computer or entirely on the remote computer or server. In the latter scenario, the remote computer may be connected in some embodiments to the user's computer through any type of network, including a LAN or a WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry in order to perform aspects of the present disclosure.

Figure 1B:
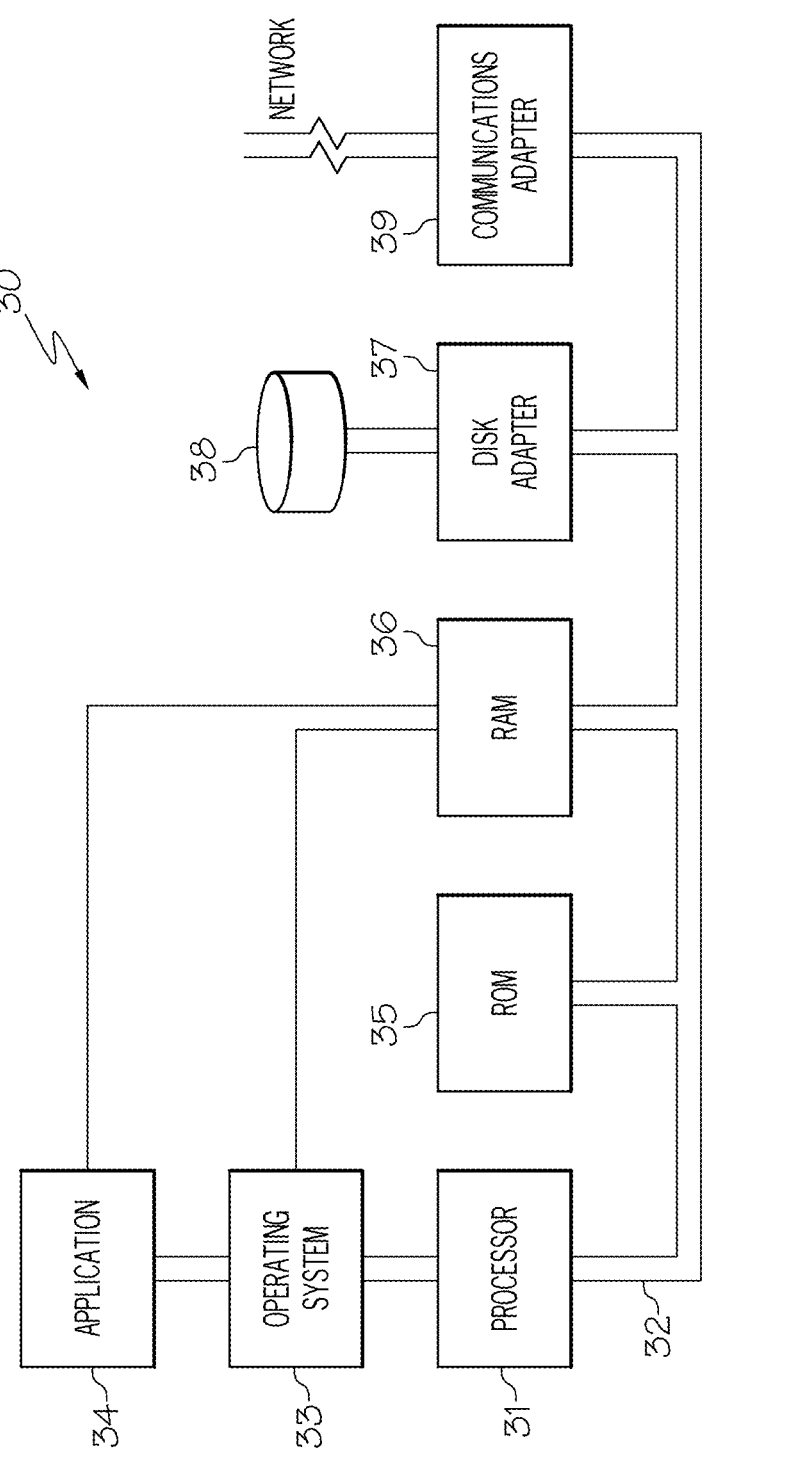
FIG. 1B illustrates a system for assessing the cardiometabolic health of a subject.
Figure 2A:
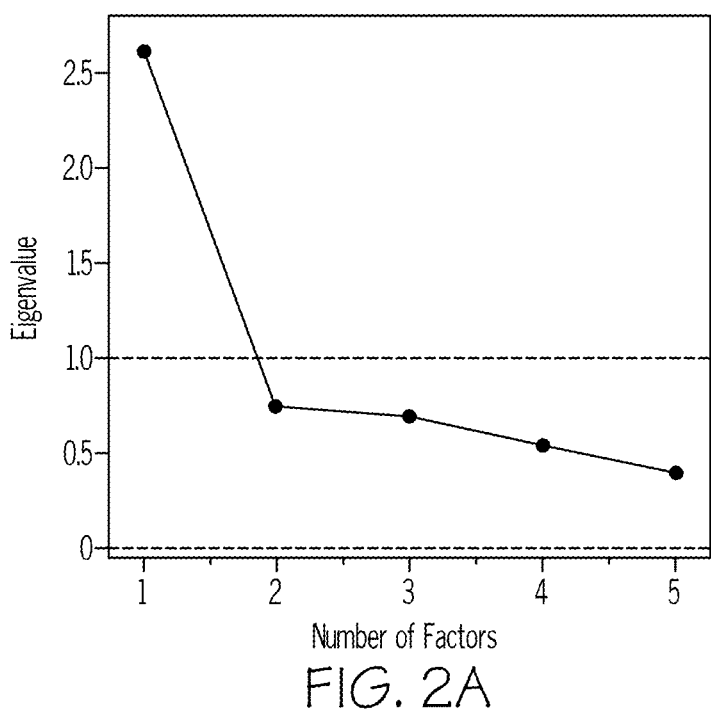
FIGS. 2A-2B provide statistical reports for the generation of latent cardiometabolic health variable CMH1, including eigenvalues (FIG. 2A) and values from a Kaiser-Meyer-Olkin test (FIG. 2B).
Figure 2B:
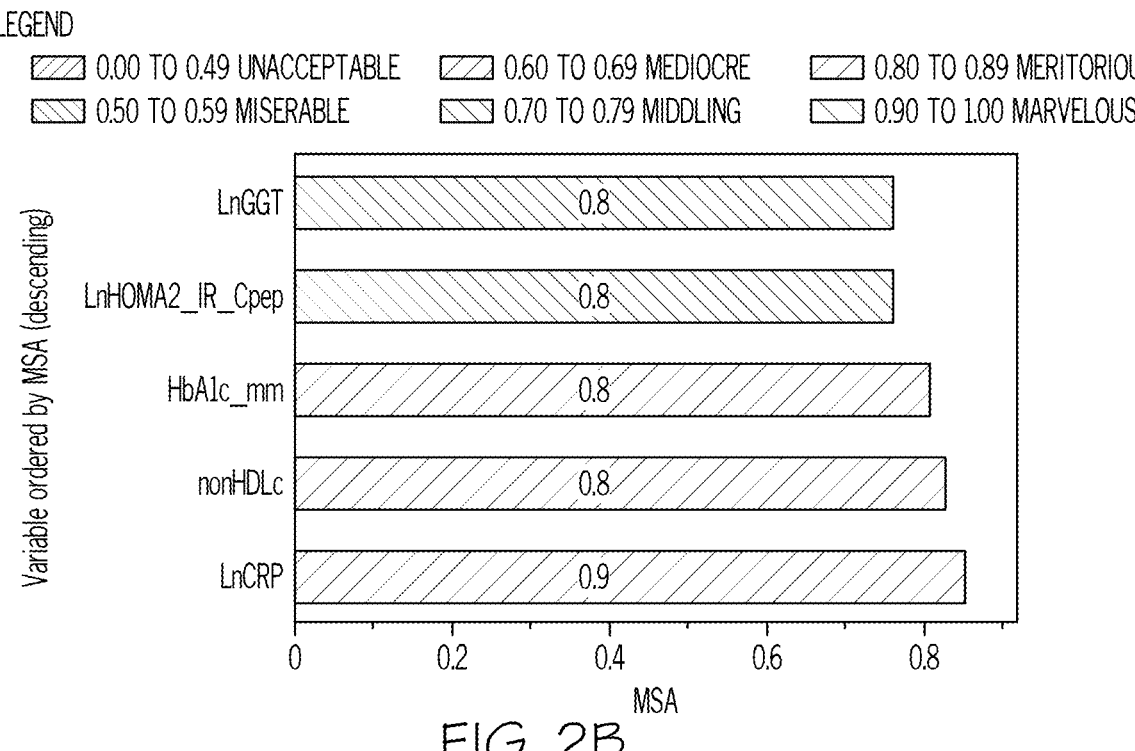
Figure 3A:
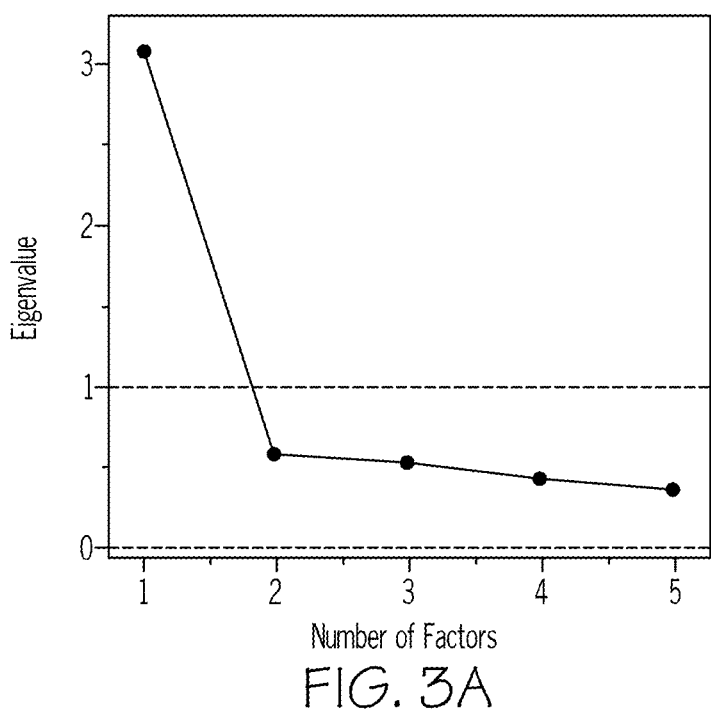
FIGS. 3A-3B provide statistical reports for the generation of latent cardiometabolic health variable CMH14, including eigenvalues (FIG. 3A) and values from a Kaiser-Meyer-Olkin test (FIG. 3B).
Figure 3B:
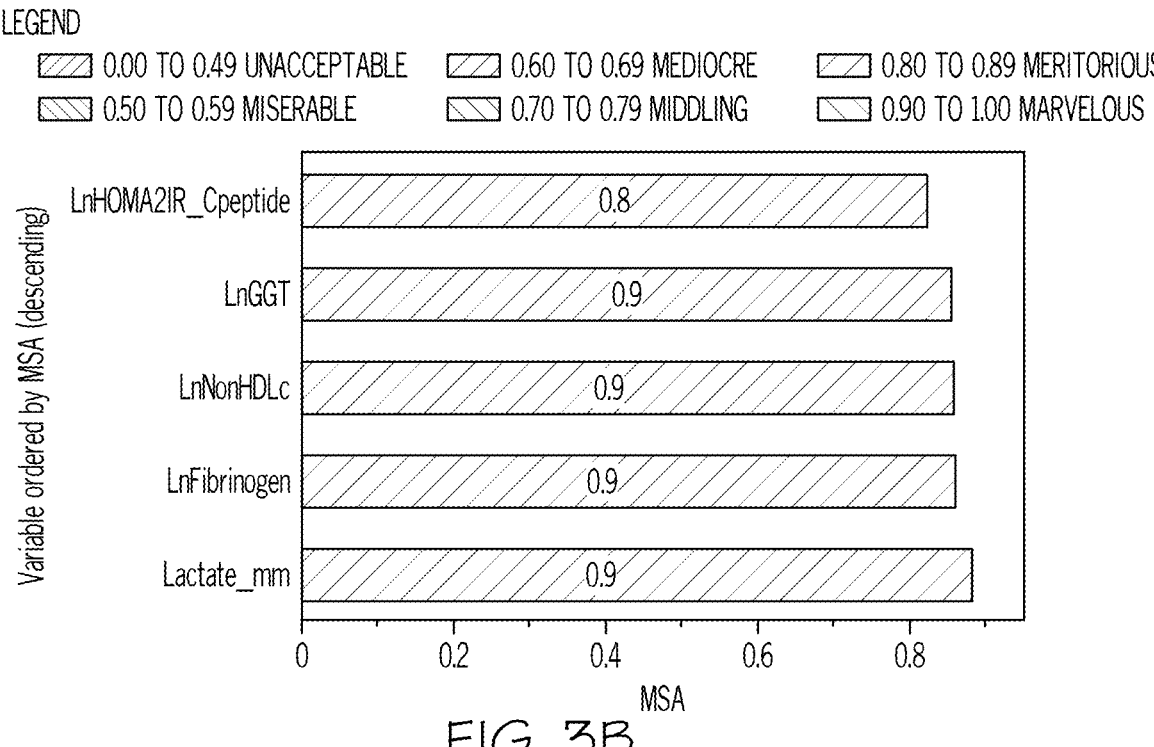
Figure 4D:
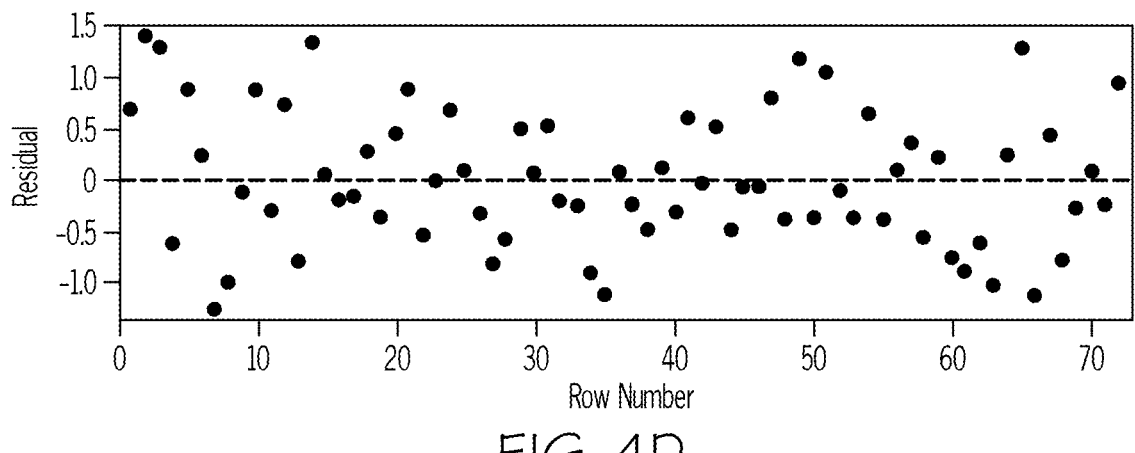
Figure 4E:
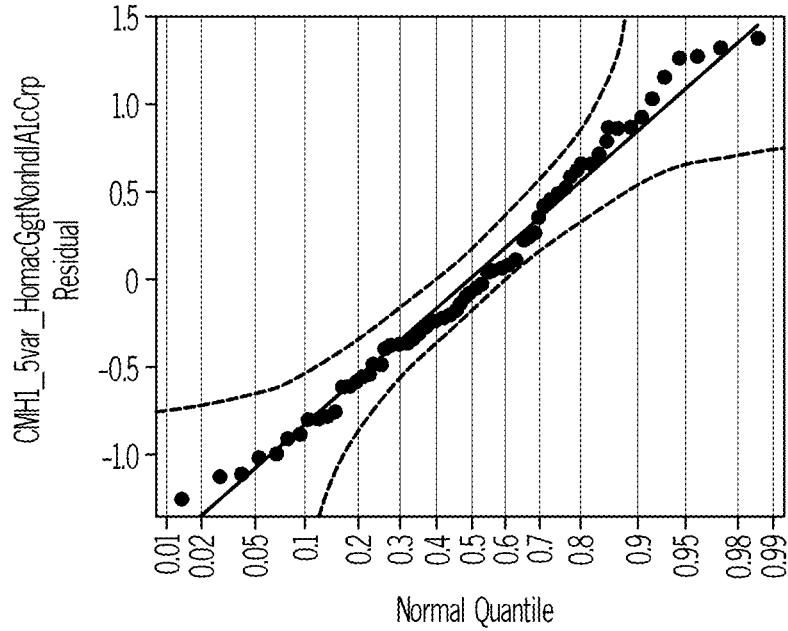
Figure 4F:
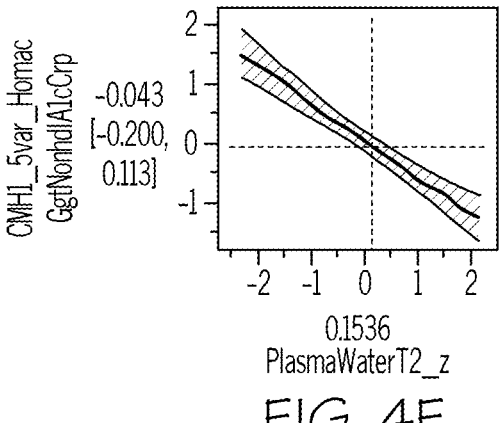
Figure 5D:
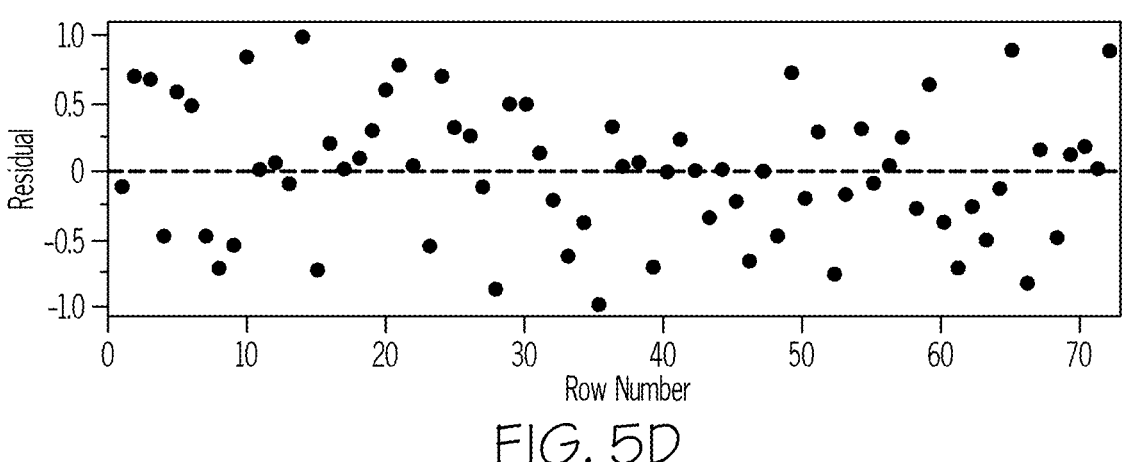
Figure 5E:
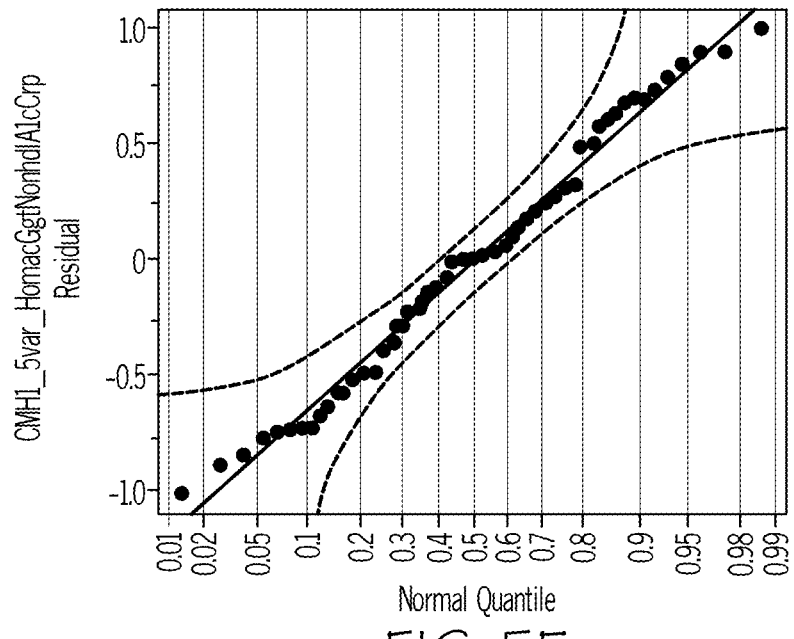
Figure 5F:
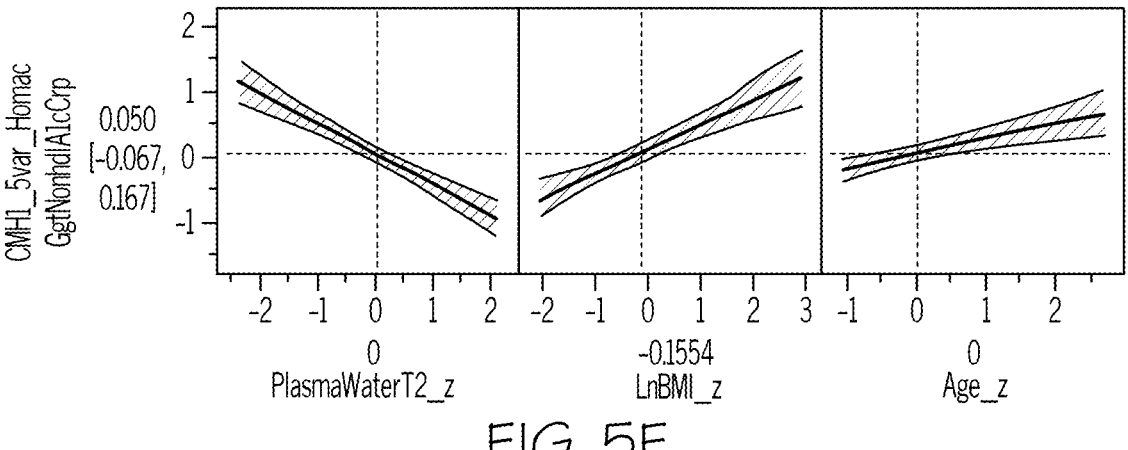
Figure 6A:
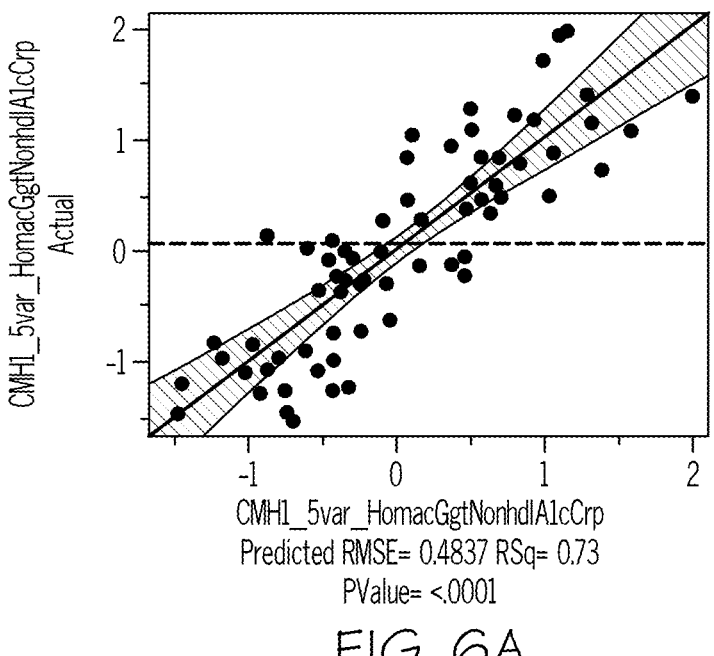
FIGS. 6A-6F provide multi-variable linear regression statistical reports for MR1C, including an actual by predicted plot (FIG. 6A), a residual by predicted plot (FIG. 6B), a studentized residuals plot (FIG. 6C), a residual by row plot (FIG. 6D), a residual normal quantile plot (FIG. 6E), and a prediction profiler (FIG. 6F).
Figure 6B:
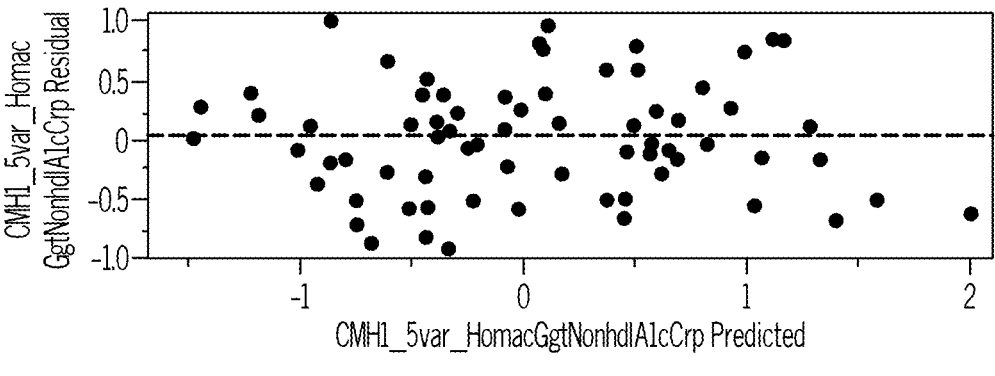
Figure 6C:
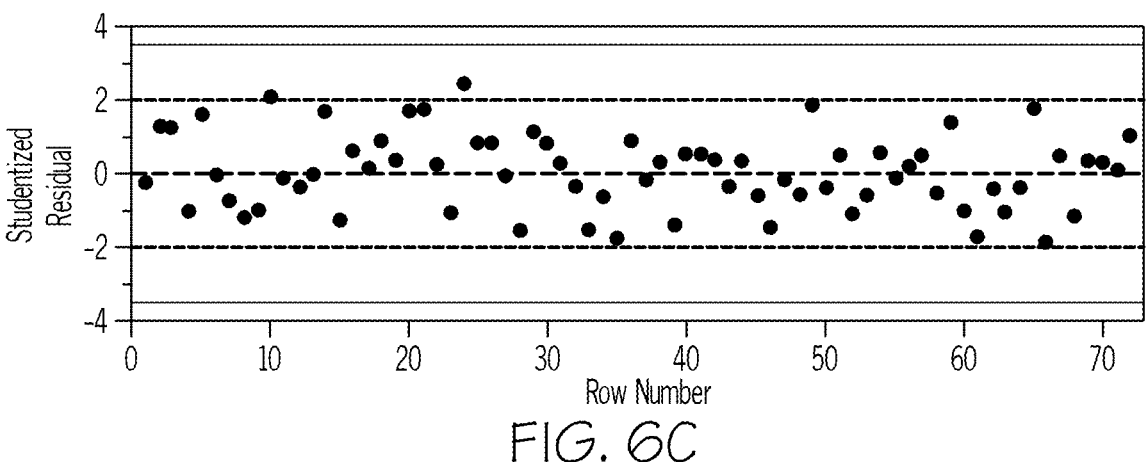
Figures 6D, 6E:
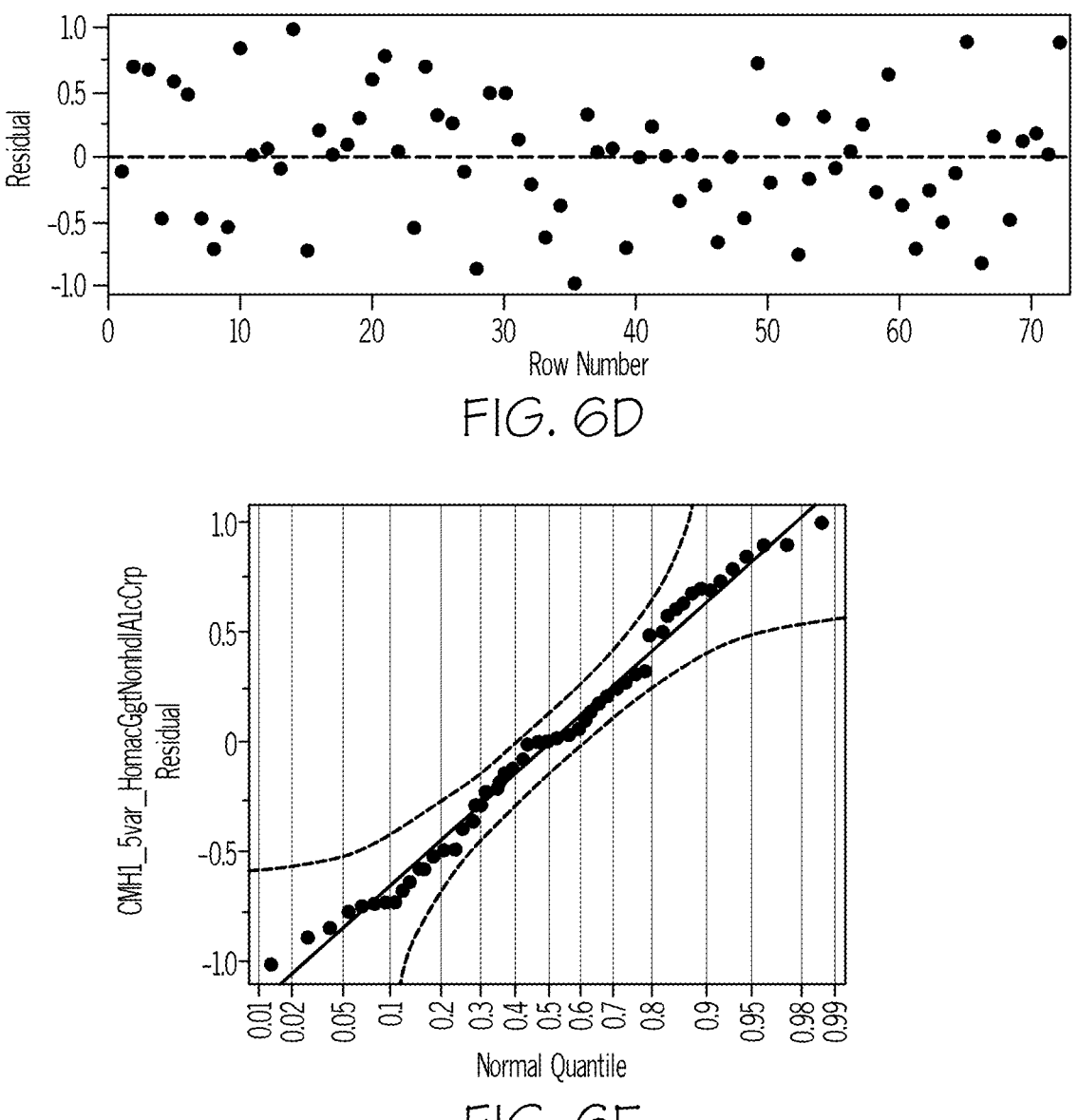
Figure 6F:
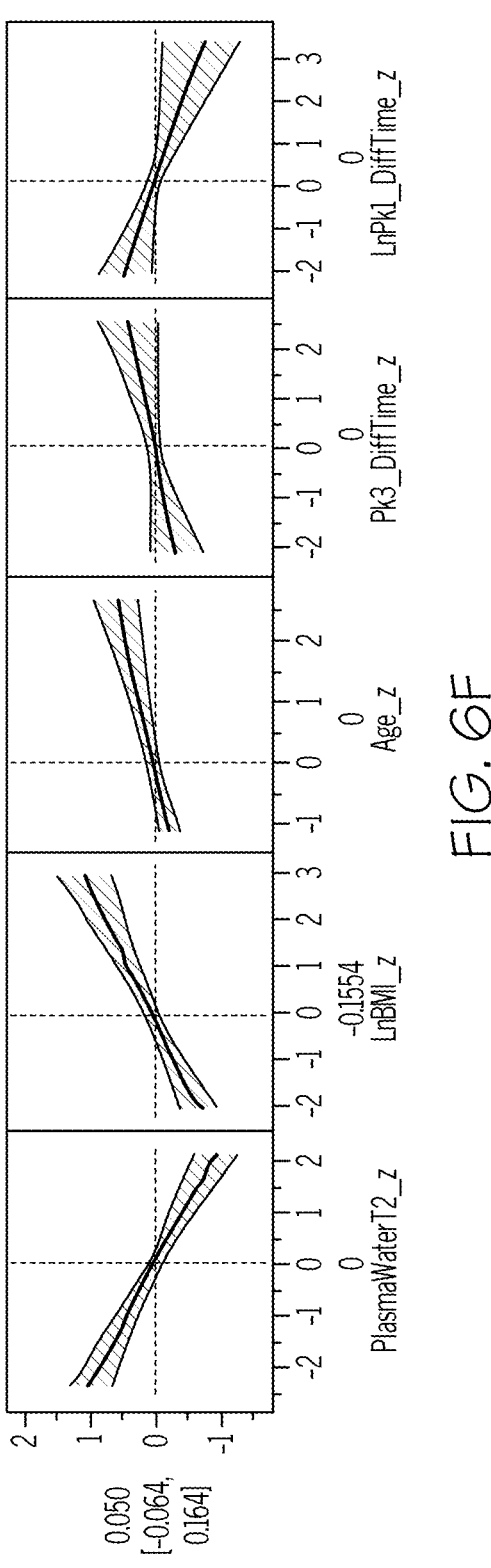
Figure 7A:
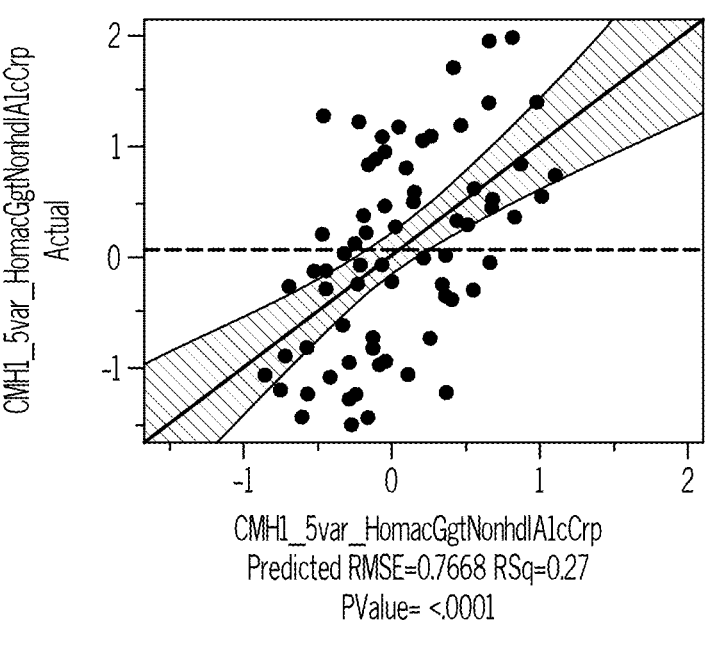
FIGS. 7A-7F provide multi-variable linear regression statistical reports for MR2A, including an actual by predicted plot (FIG. 7A), a residual by predicted plot (FIG. 7B), a studentized residuals plot (FIG. 7C), a residual by row plot (FIG. 7D), a residual normal quantile plot (FIG. 7E), and a prediction profiler (FIG. 7F).
Figure 7B:
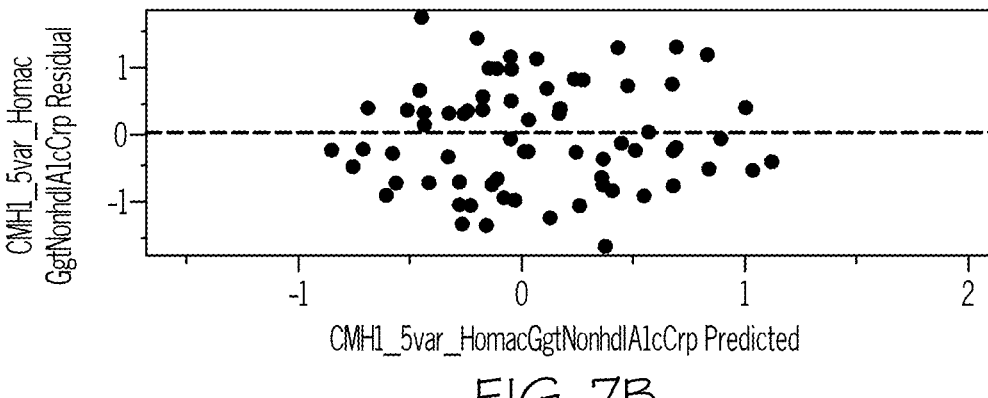
Figure 7C:
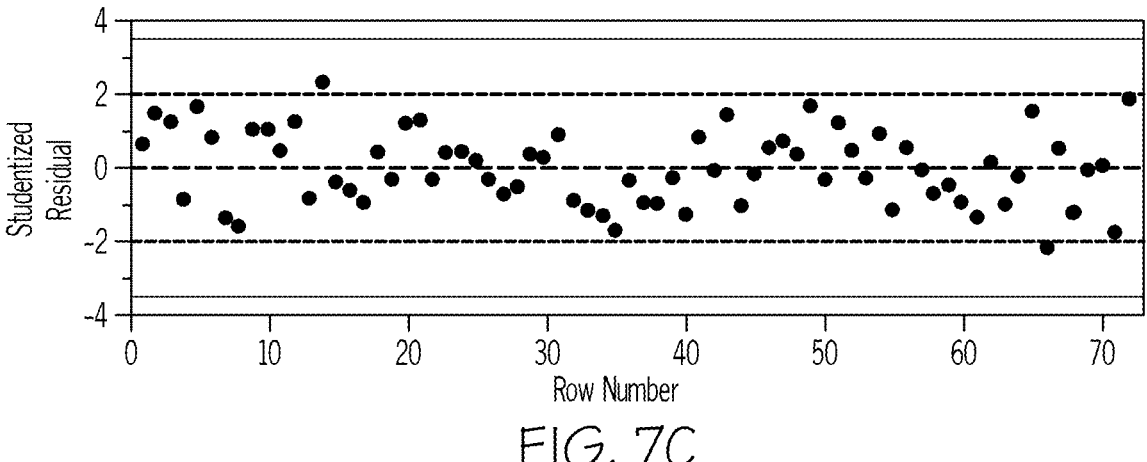
Figure 7D:
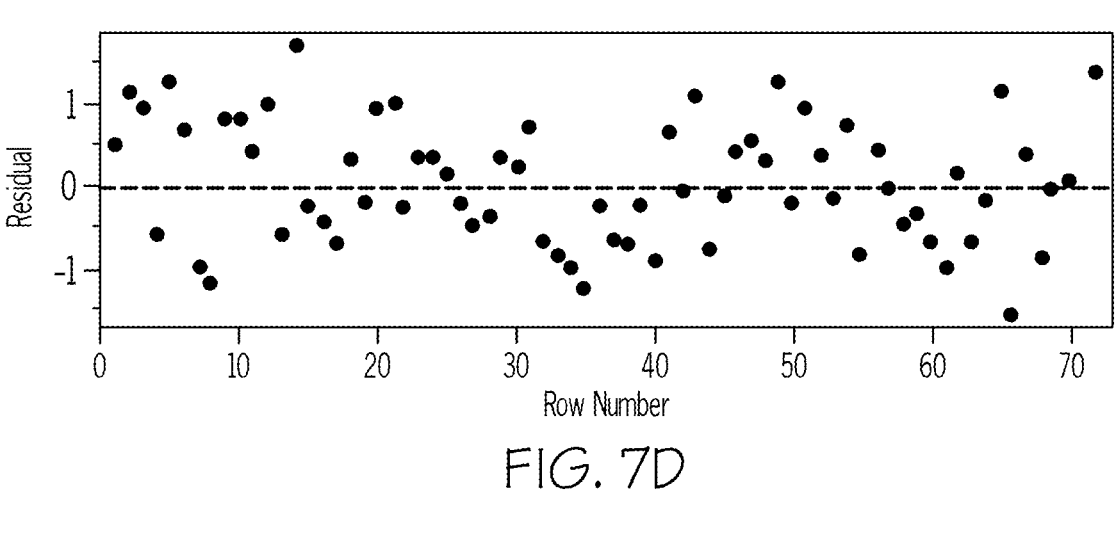
Figure 7E:
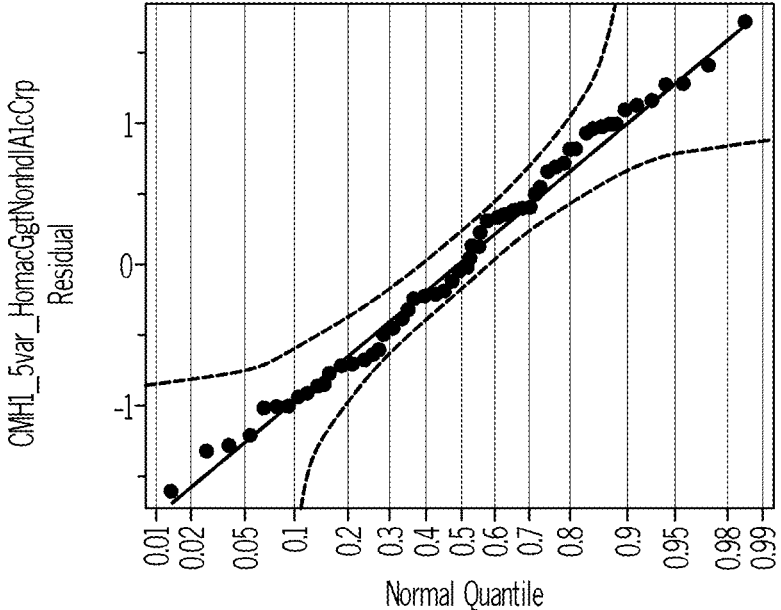
Figure 7F:
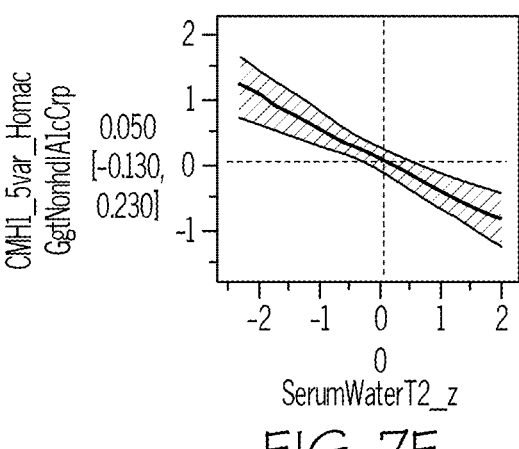
Figure 8A:
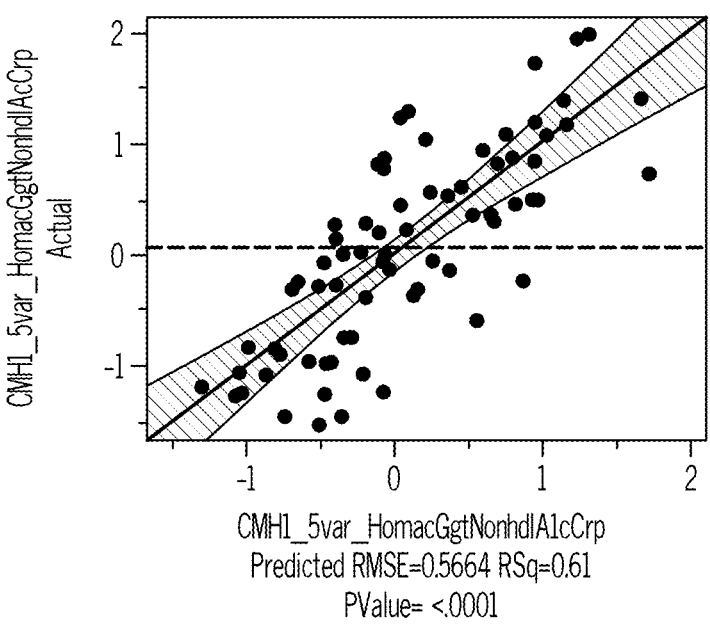
FIGS. 8A-8F provide multi-variable linear regression statistical reports for MR2B, including an actual by predicted plot (FIG. 8A), a residual by predicted plot (FIG. 8B), a studentized residuals plot (FIG. 8C), a residual by row plot (FIG. 8D), a residual normal quantile plot (FIG. 8E), and a prediction profiler (FIG. 8F).
Figure 8B:
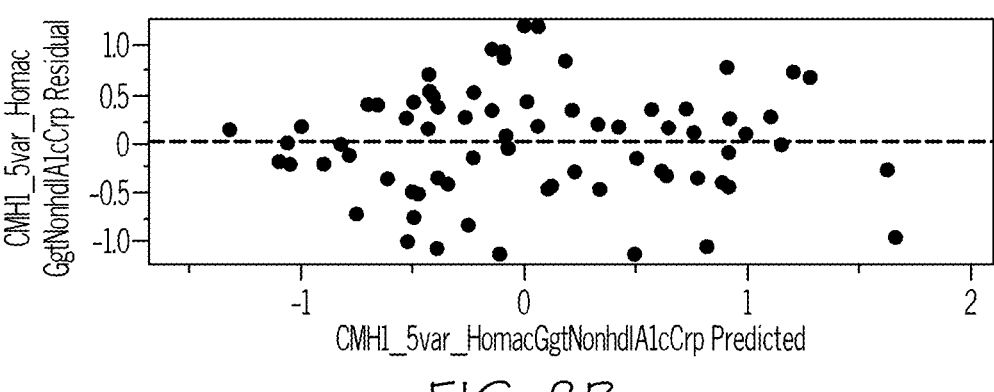
Figure 8C:
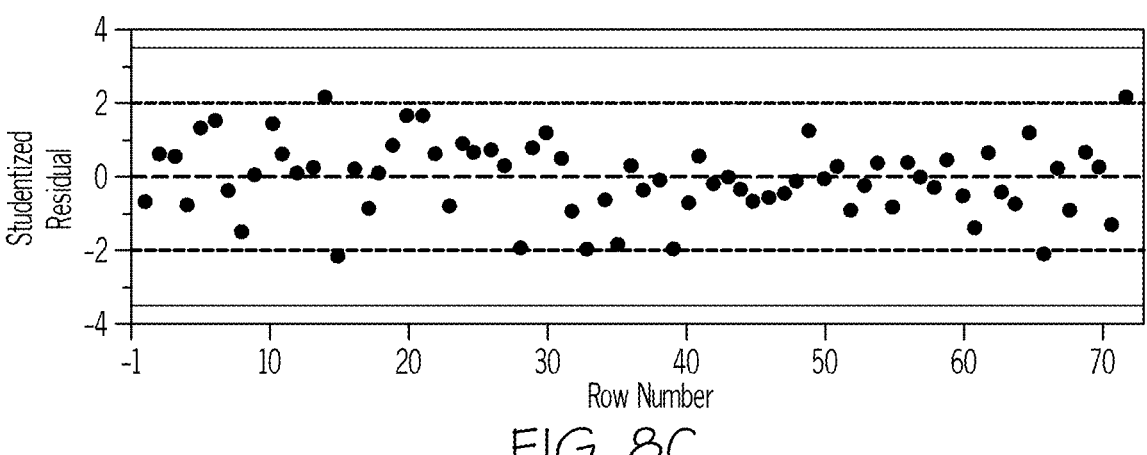
Figure 8D:
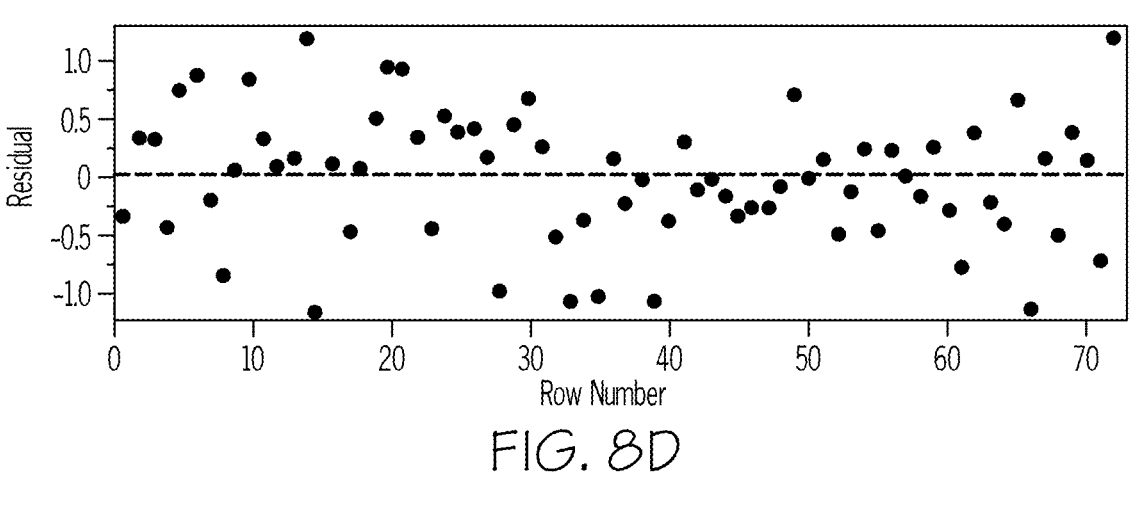
Figure 8E:
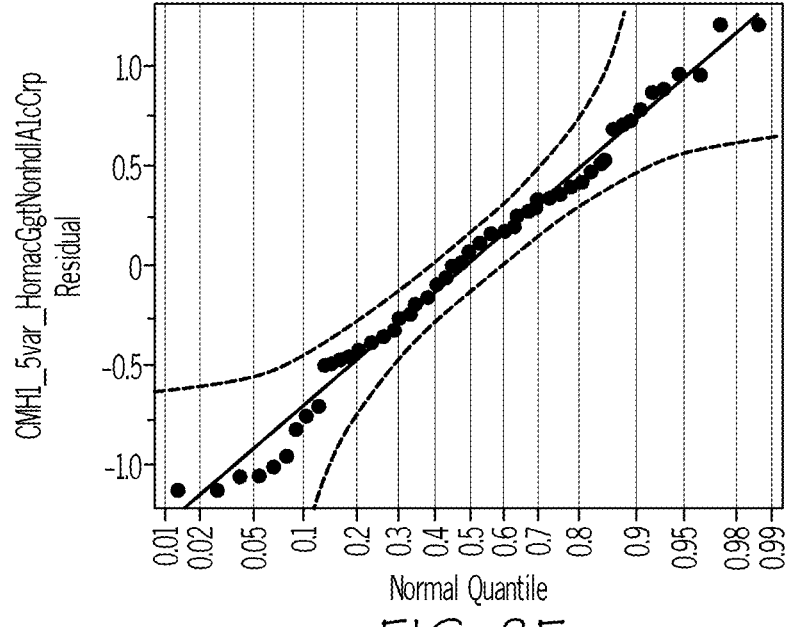
Figure 8F:
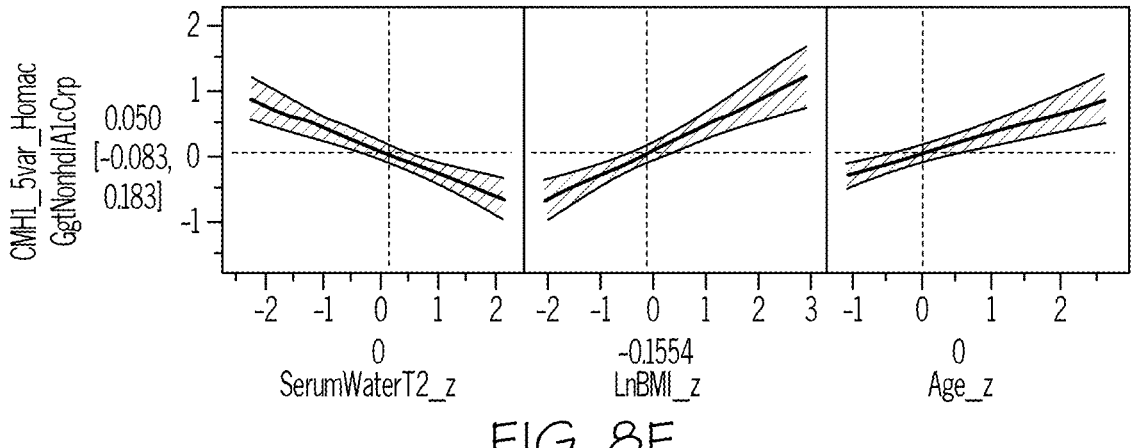
Figure 9A:
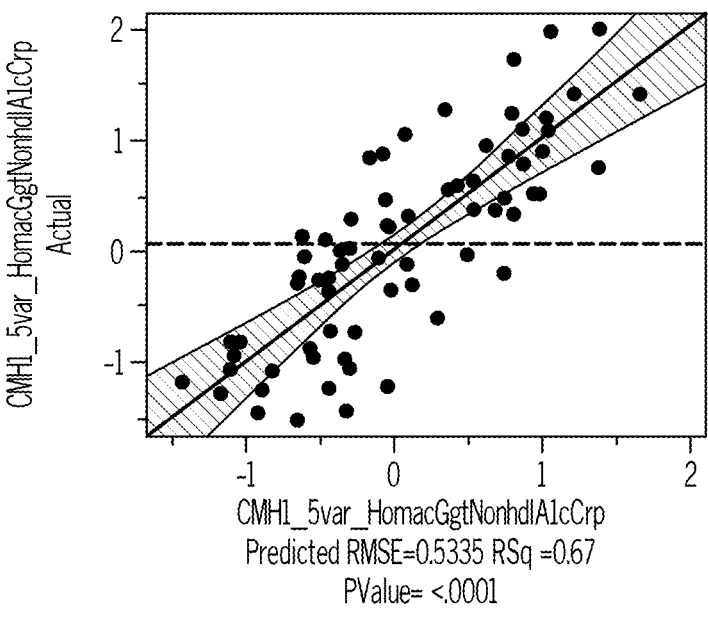
FIGS. 9A-9F provide multi-variable linear regression statistical reports for MR2C, including an actual by predicted plot (FIG. 9A), a residual by predicted plot (FIG. 9B), a studentized residuals plot (FIG. 9C), a residual by row plot (FIG. 9D), a residual normal quantile plot (FIG. 9E), and a prediction profiler (FIG. 9F).
Figure 9B:
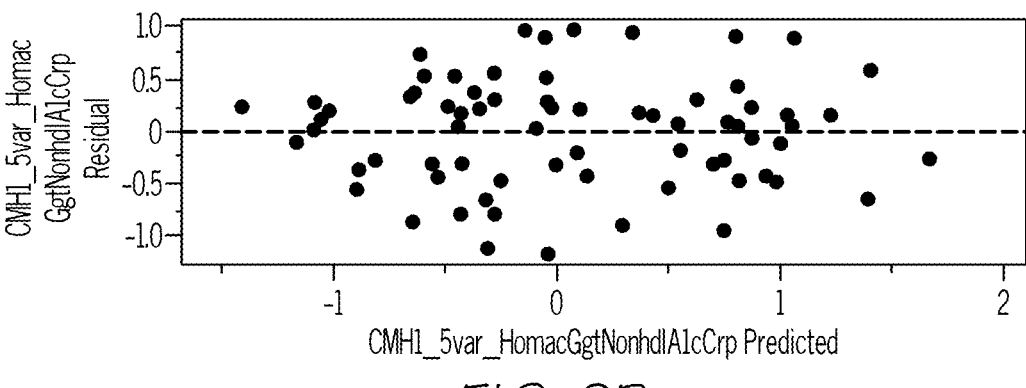
Figure 9C:
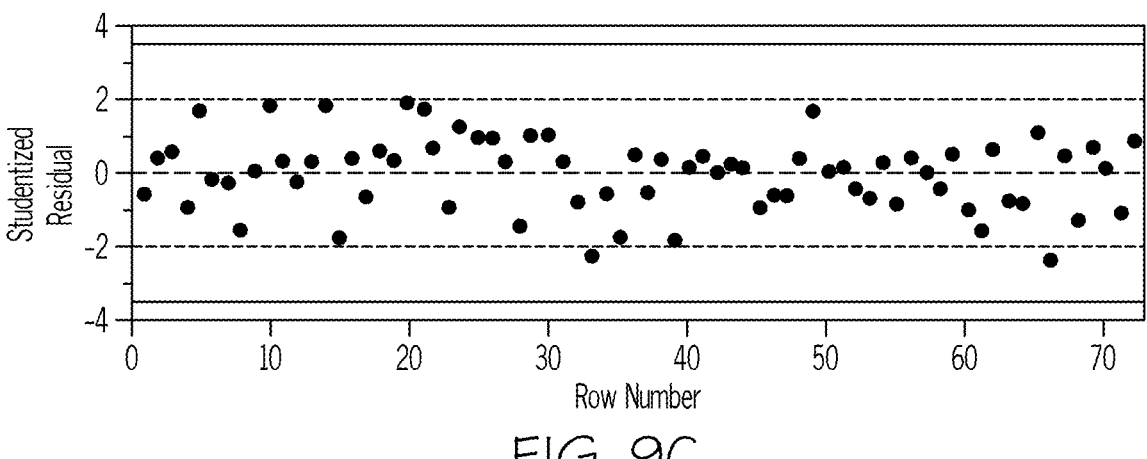
Figure 9D:
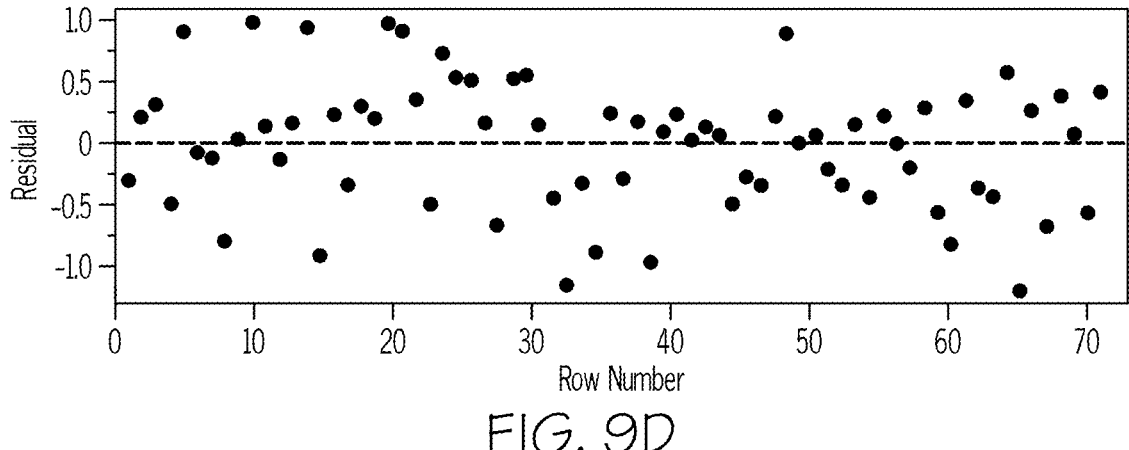
Figure 9E:
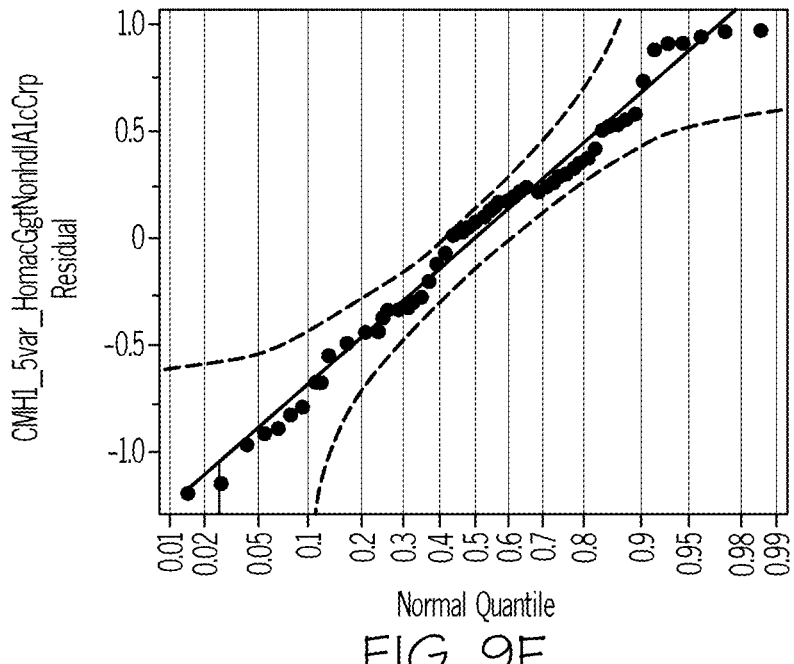
Figure 9F:
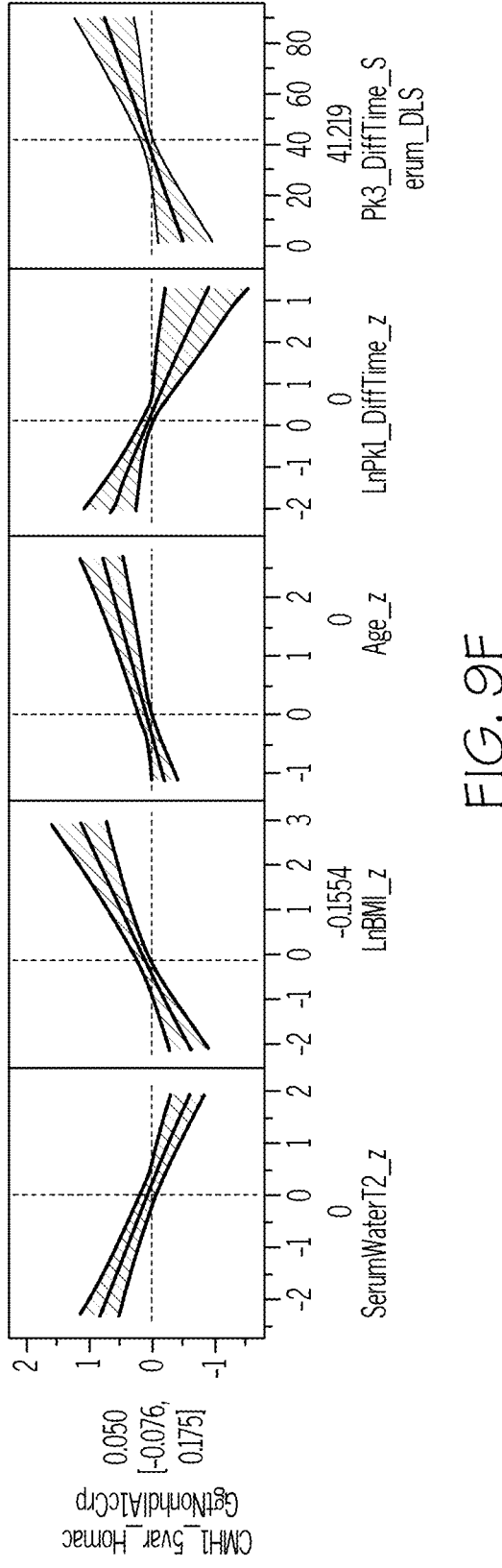
Figure 10A:
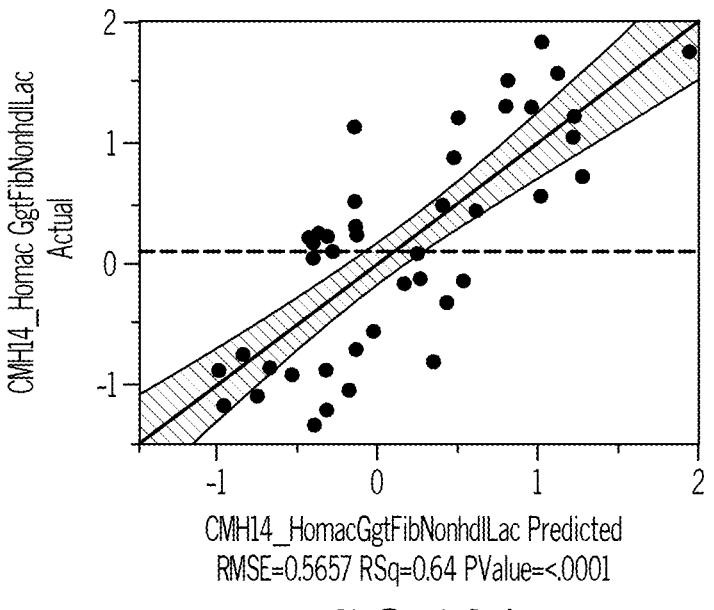
FIGS. 10A-10F provide multi-variable linear regression statistical reports for MR3A, including an actual by predicted plot (FIG. 10A), a residual by predicted plot (FIG. 10B), a studentized residuals plot (FIG. 10C), a residual by row plot (FIG. 10D), a residual normal quantile plot (FIG. 10E), and a prediction profiler (FIG. 10F).
Figure 10B:
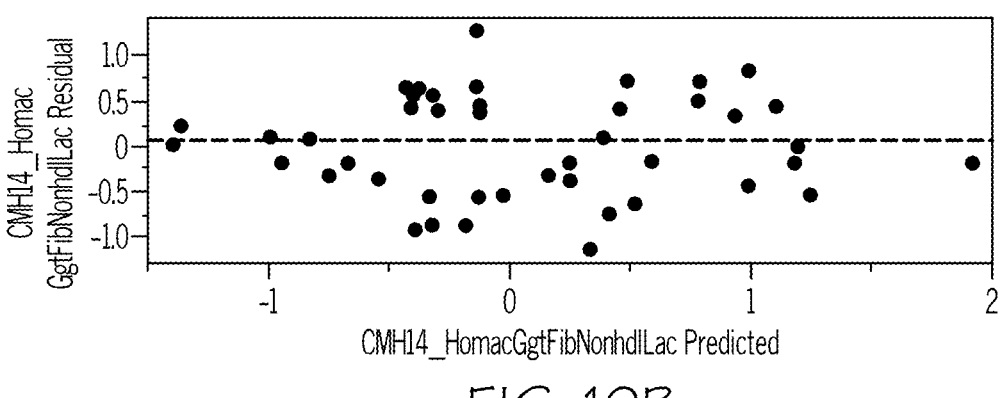
Figure 10C:
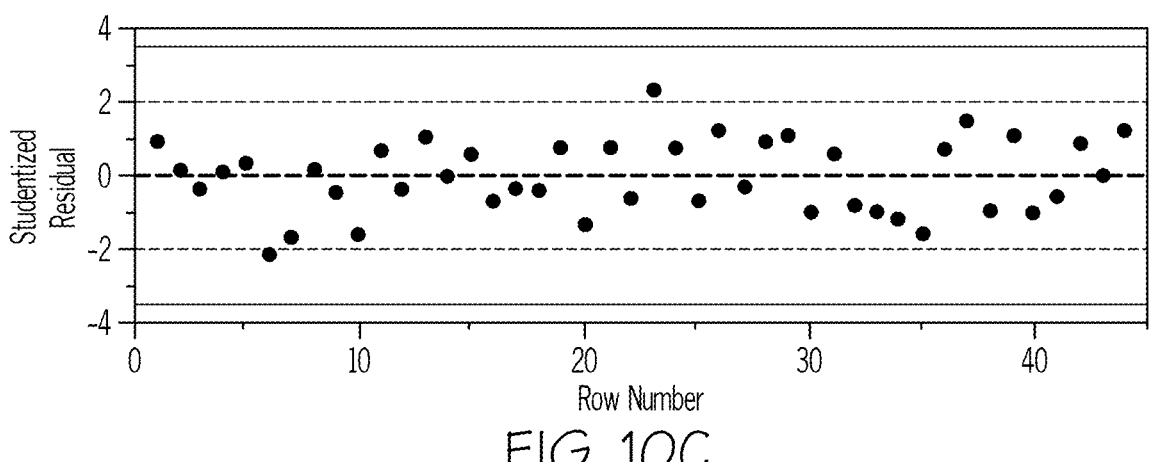
Figure 10D:
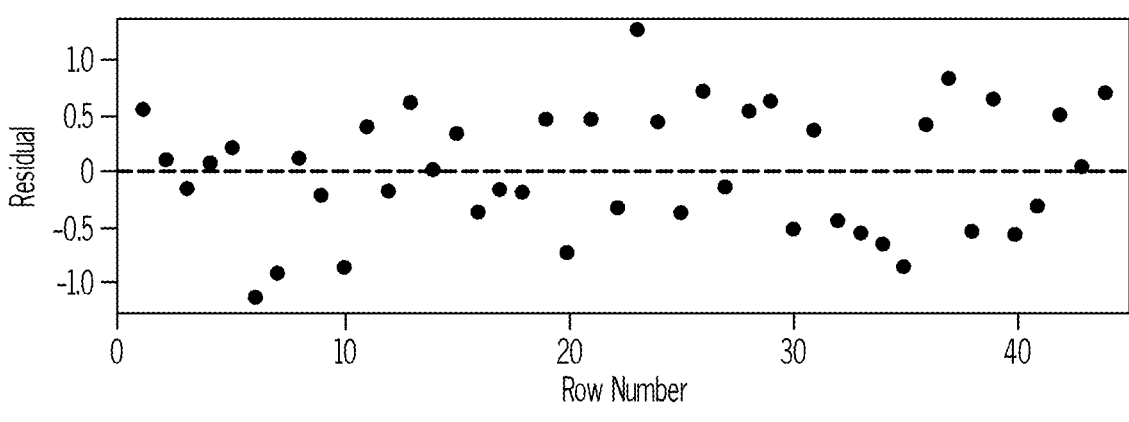
Figure 10E:
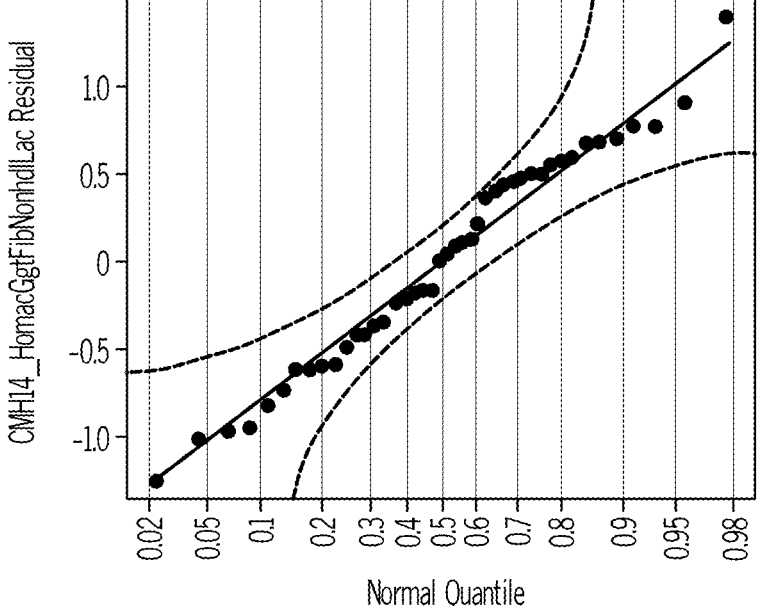
Figure 10F:
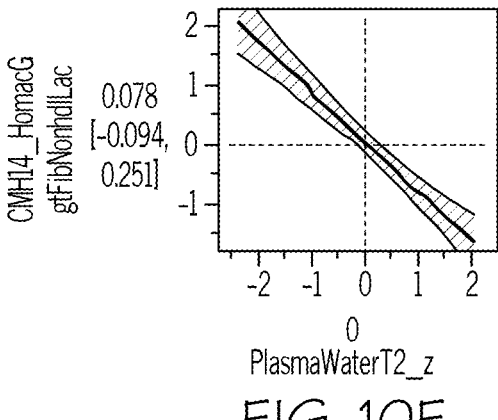
Figure 11A:
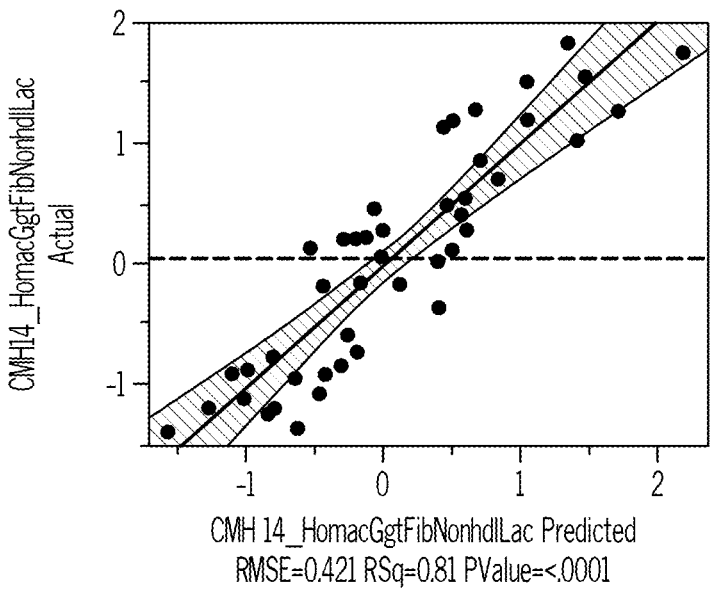
FIGS. 11A-11F provide multi-variable linear regression statistical reports for MR3B, including an actual by predicted plot (FIG. 11A), a residual by predicted plot (FIG. 11B), a studentized residuals plot (FIG. 11C), a residual by row plot (FIG. 11D), a residual normal quantile plot (FIG. 11E), and a prediction profiler (FIG. 11F).
Figure 11B:
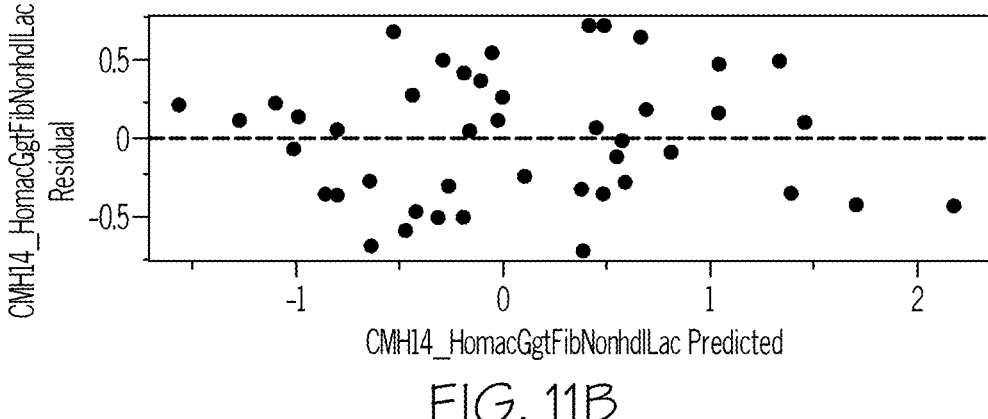
Figure 11C:
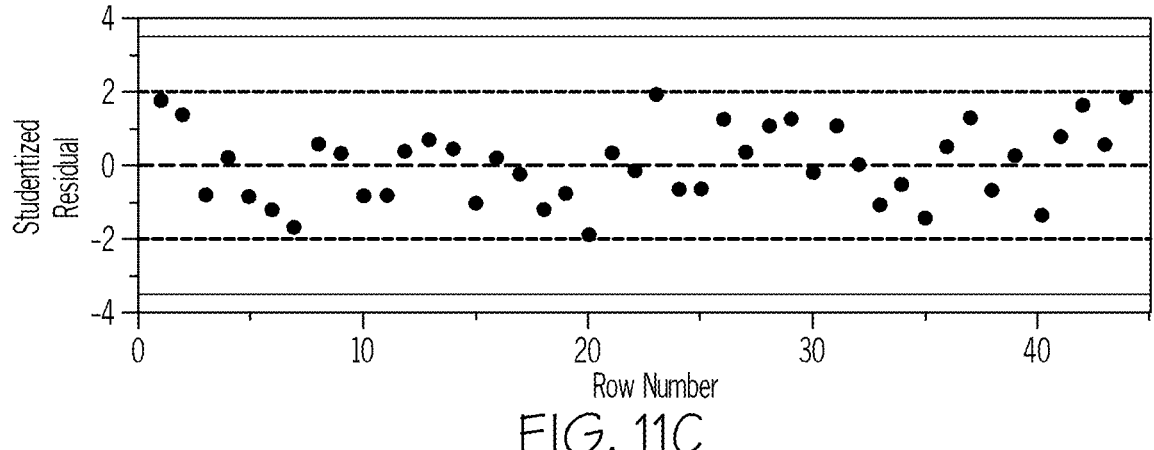
Figures 11D, 11E:
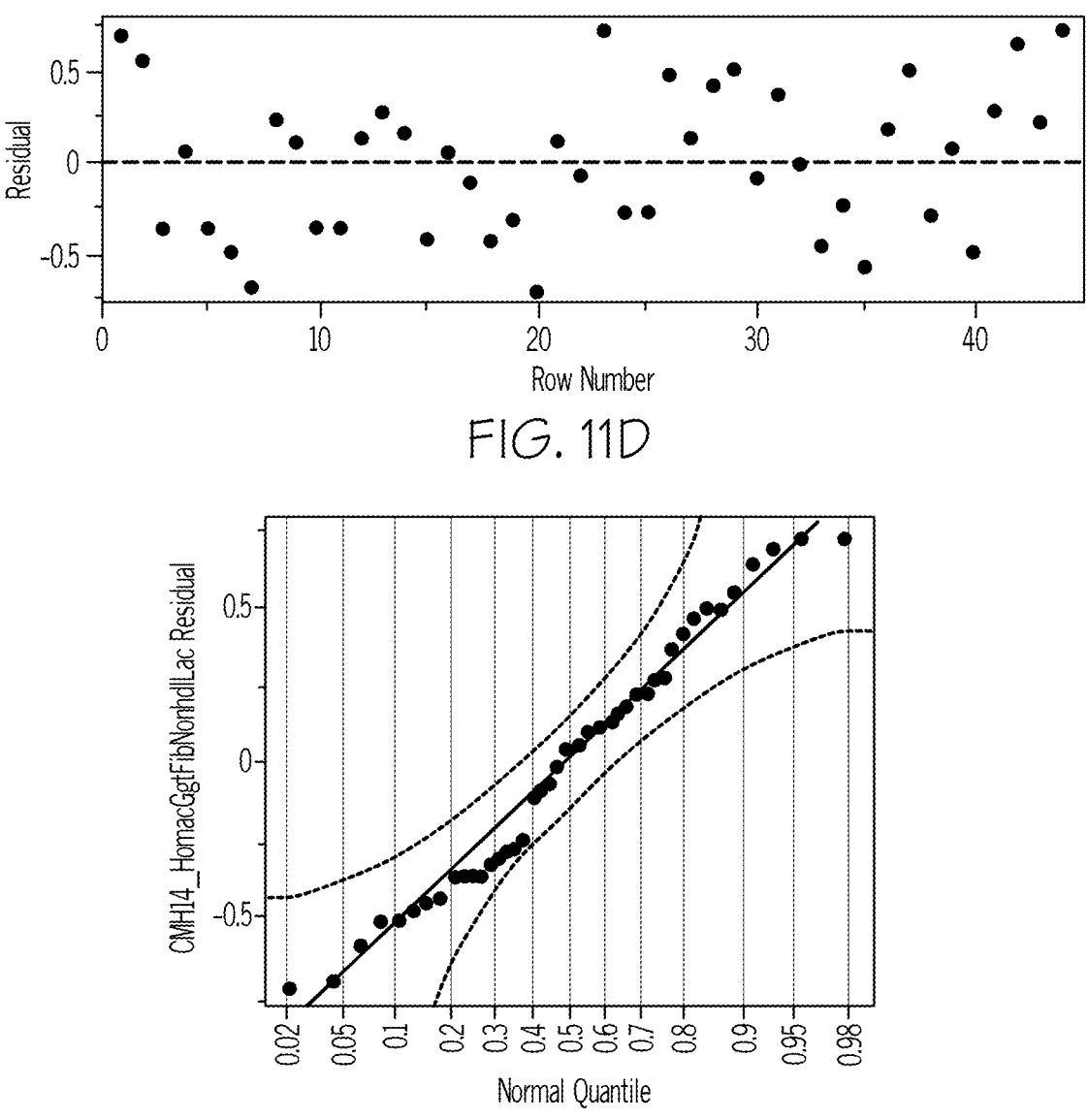
Figure 11F:
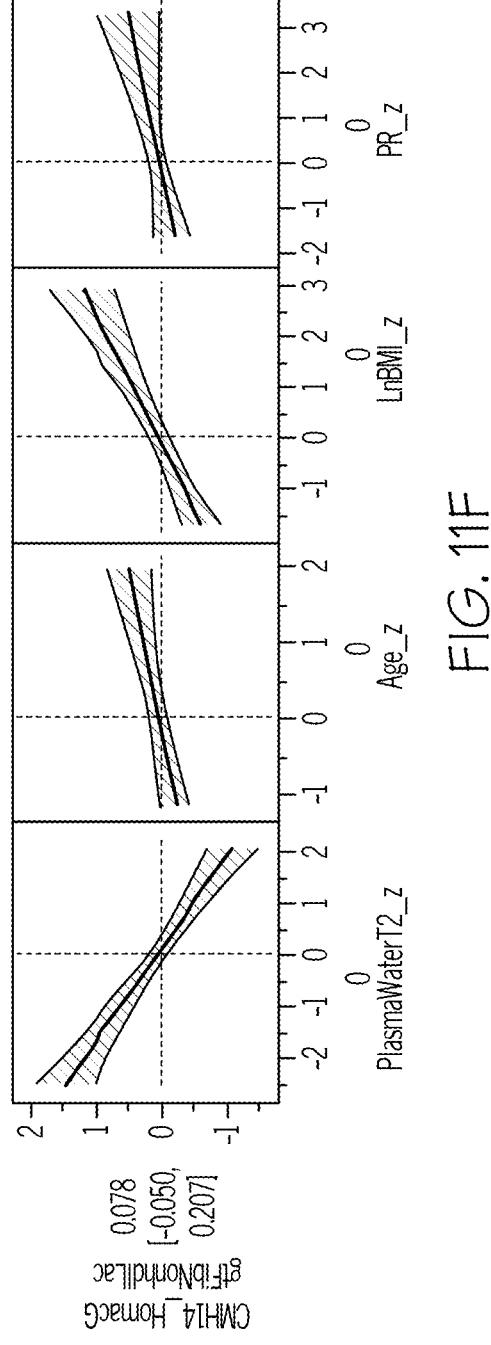
Figures 12D, 12E:
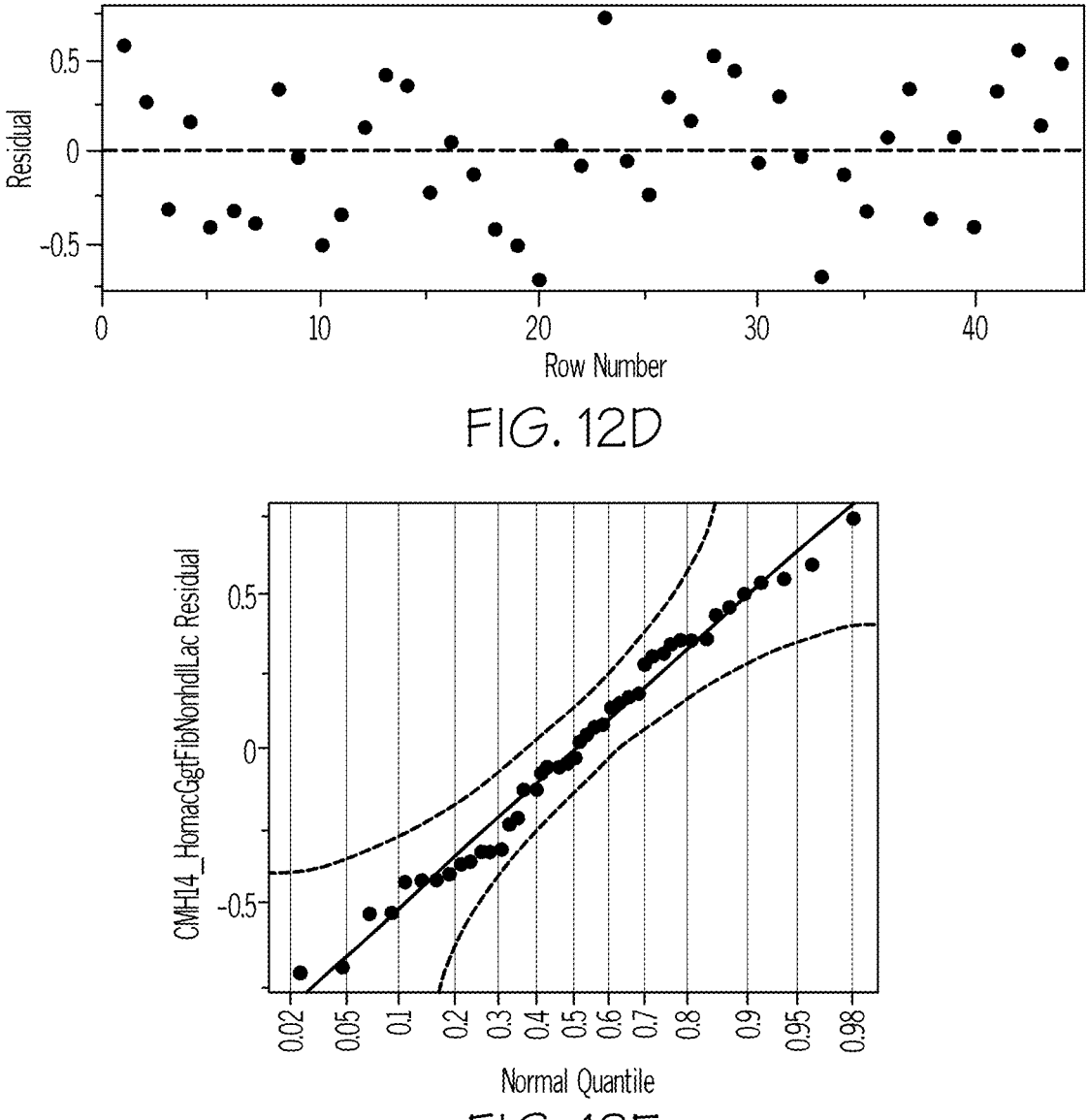
Figure 12F:
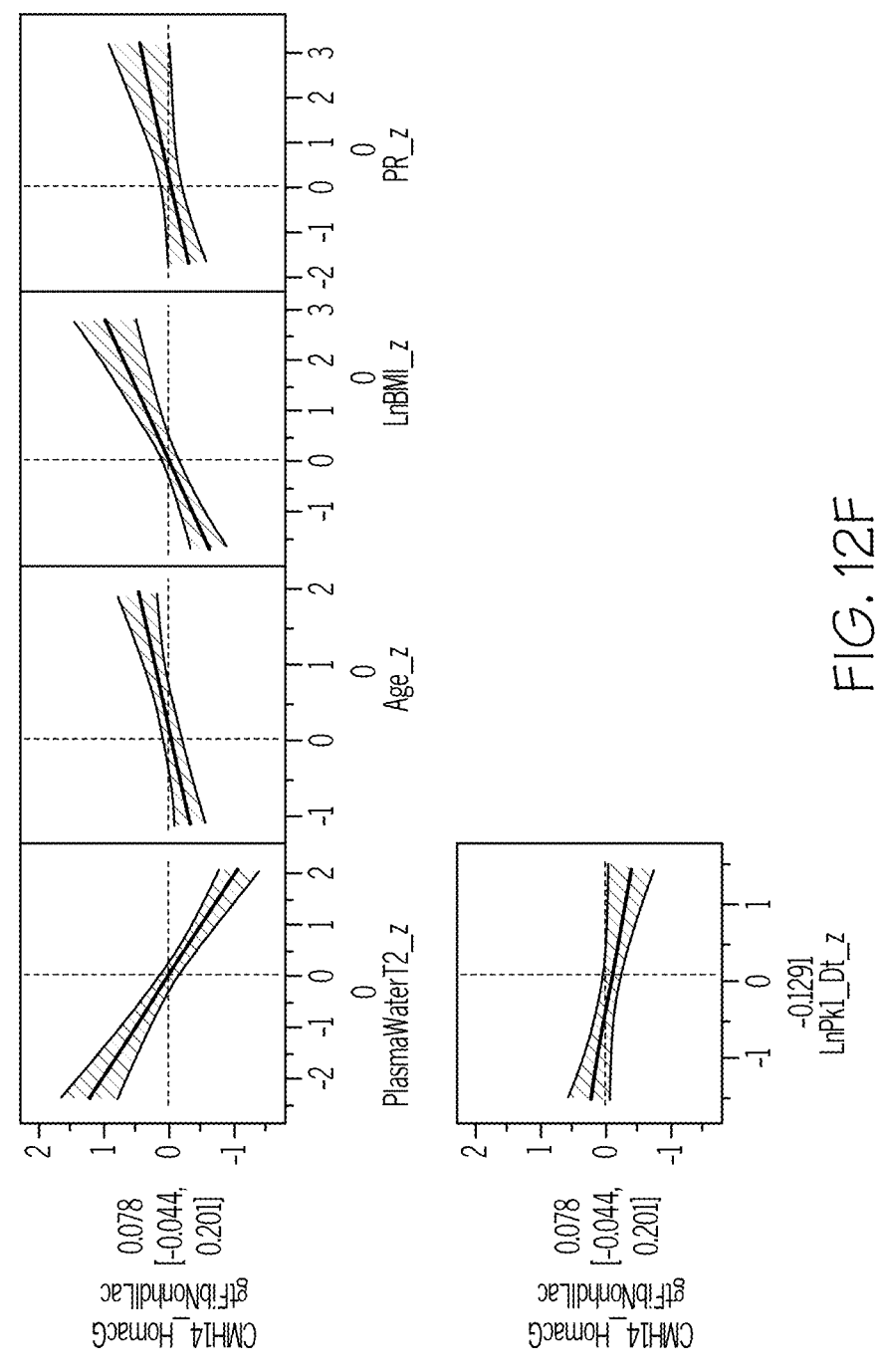
Figure 13A:
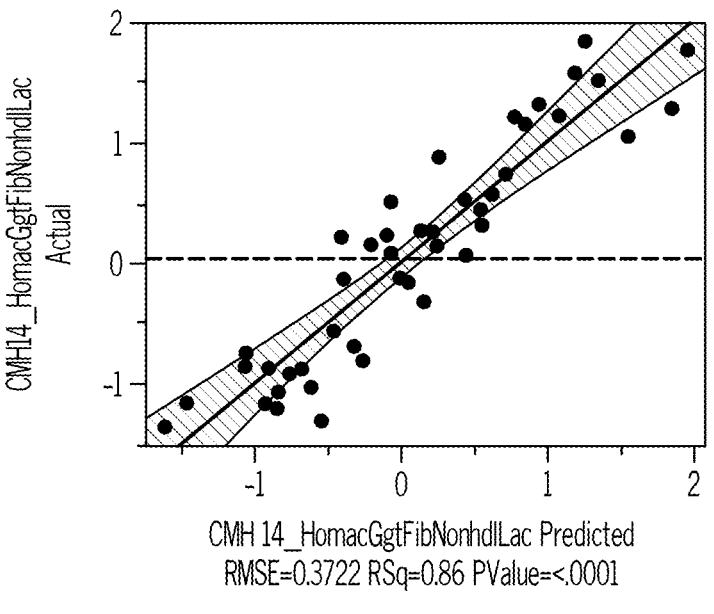
FIGS. 13A-13F provide multi-variable linear regression statistical reports for MR3D, including an actual by predicted plot (FIG. 13A), a residual by predicted plot (FIG. 13B), a studentized residuals plot (FIG. 13C), a residual by row plot (FIG. 13D), a residual normal quantile plot (FIG. 13E), and a prediction profiler (FIG. 13F).
Figure 13B:
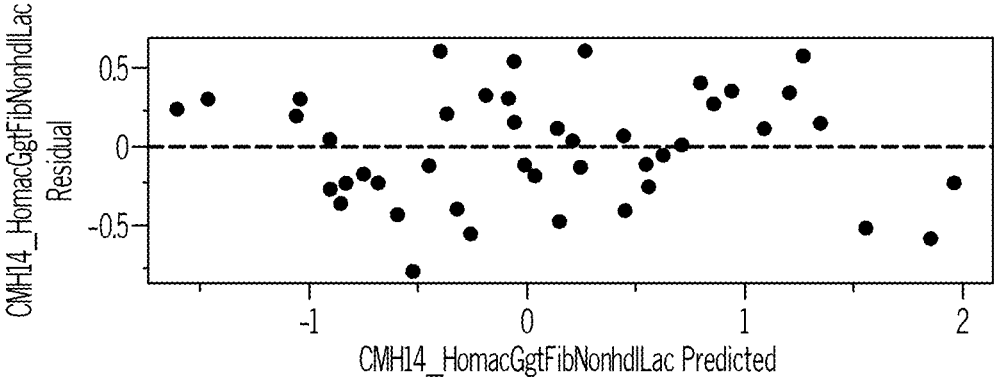
Figure 13C:
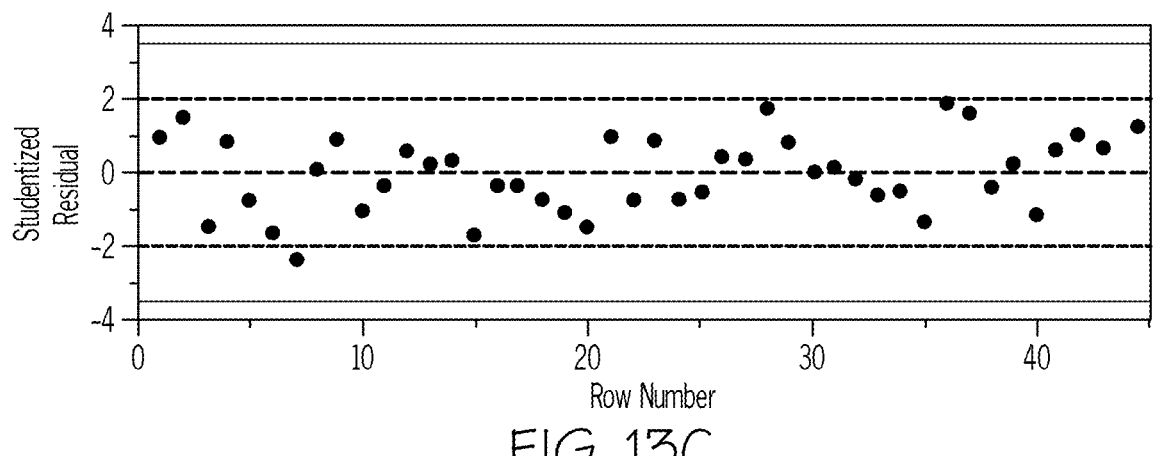
Figures 13D, 13E:
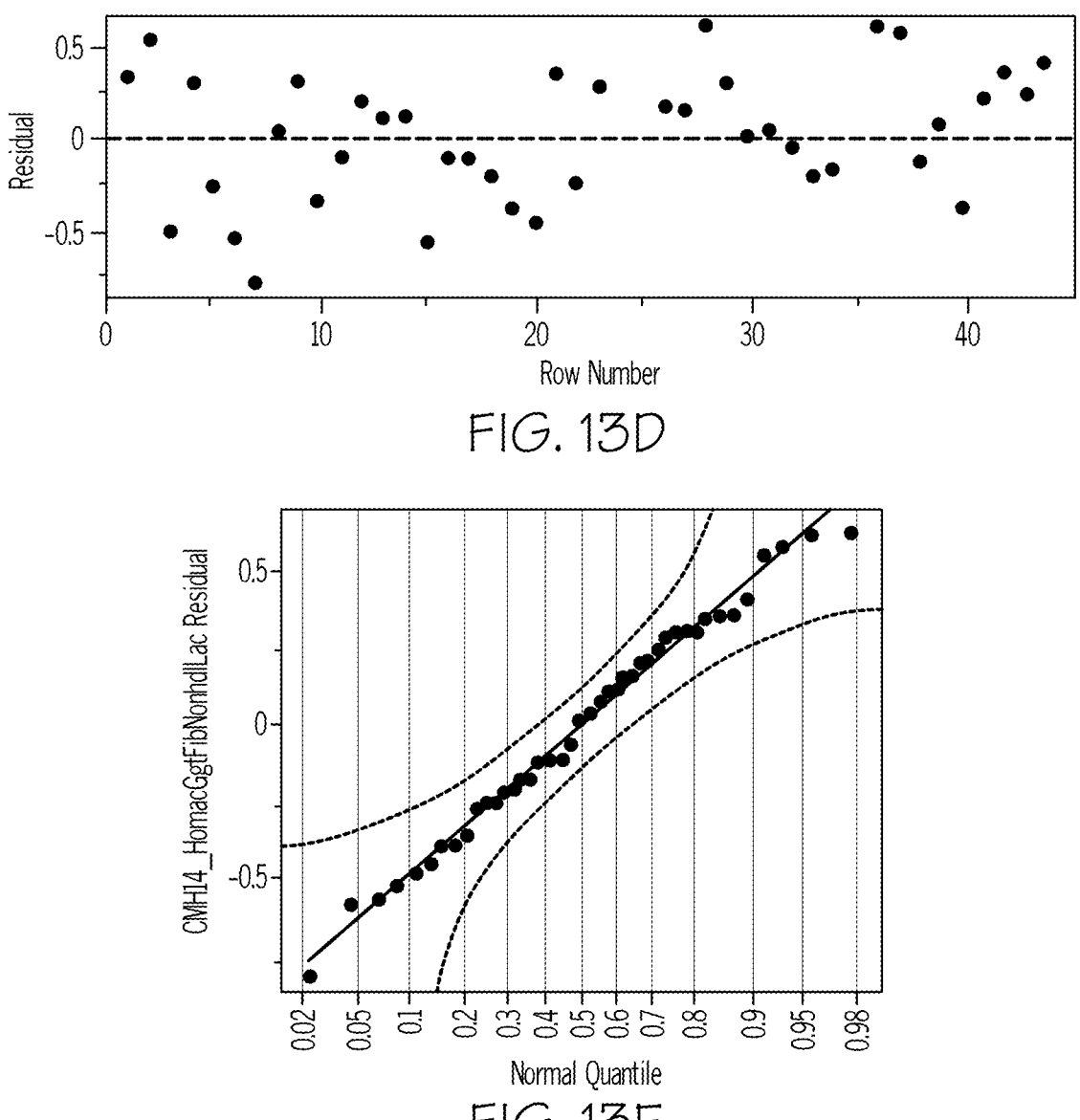
Figure 13F:
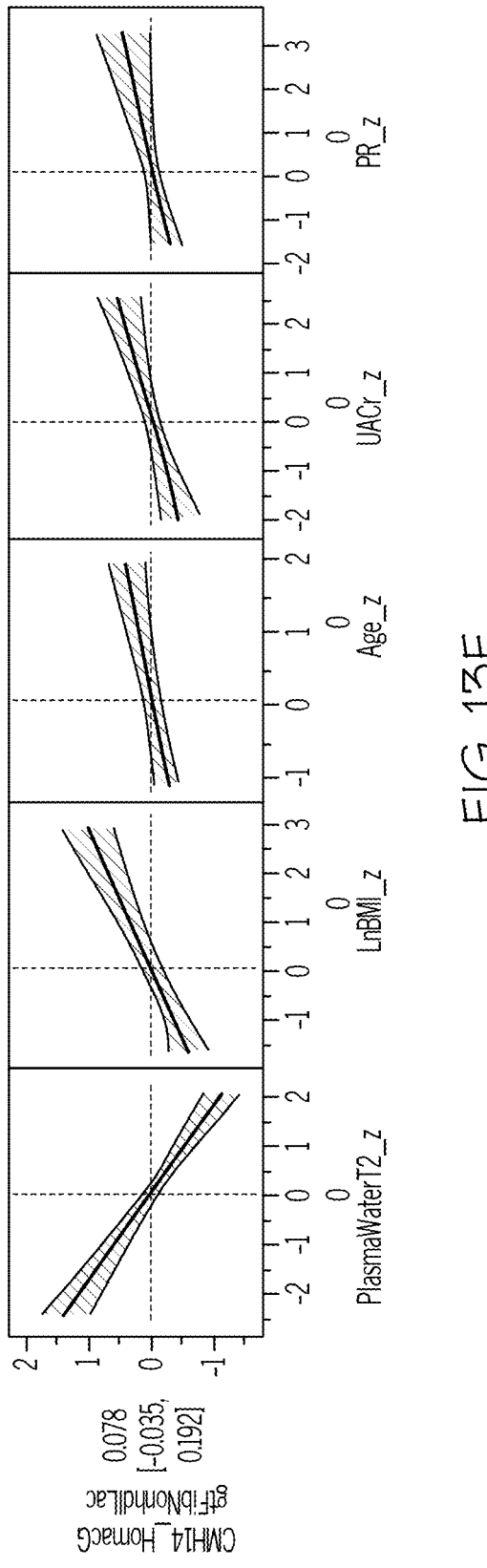
Figure 14A:
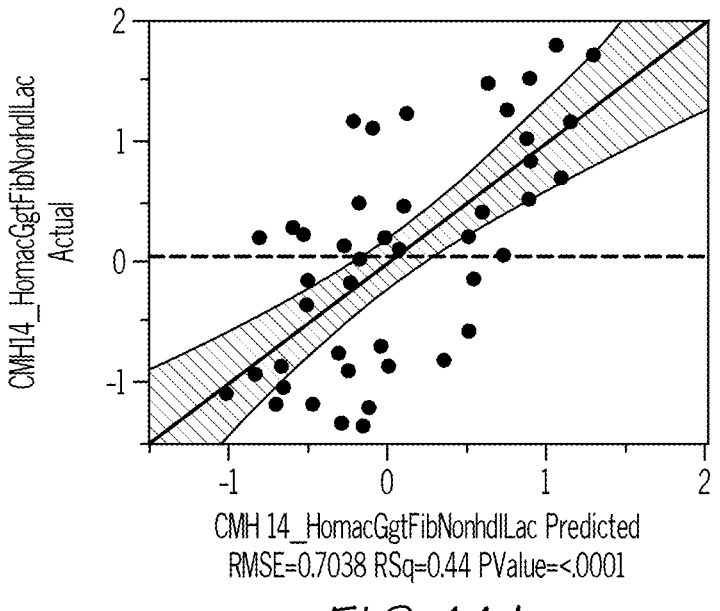
FIGS. 14A-14F provide multi-variable linear regression statistical reports for MR4A, including an actual by predicted plot (FIG. 14A), a residual by predicted plot (FIG. 14B), a studentized residuals plot (FIG. 14C), a residual by row plot (FIG. 14D), a residual normal quantile plot (FIG. 14E), and a prediction profiler (FIG. 14F).
Figure 14B:
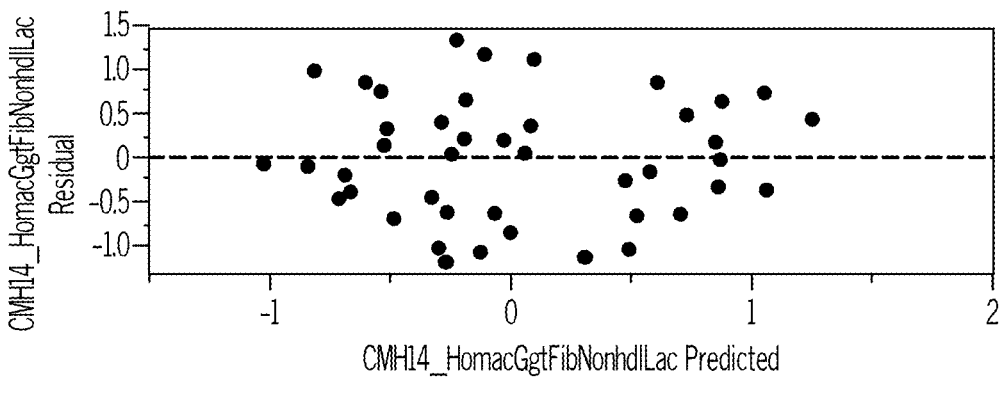
Figure 14C:
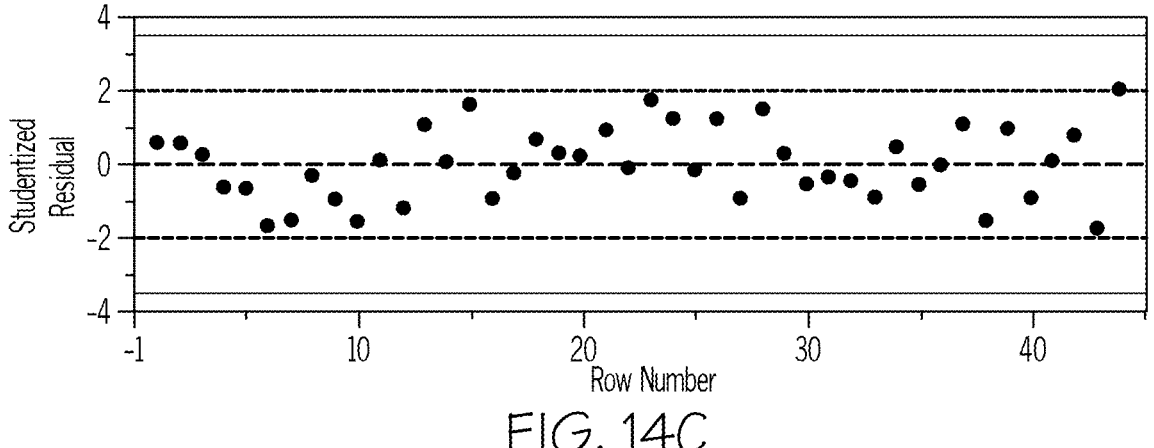
Figure 14D:
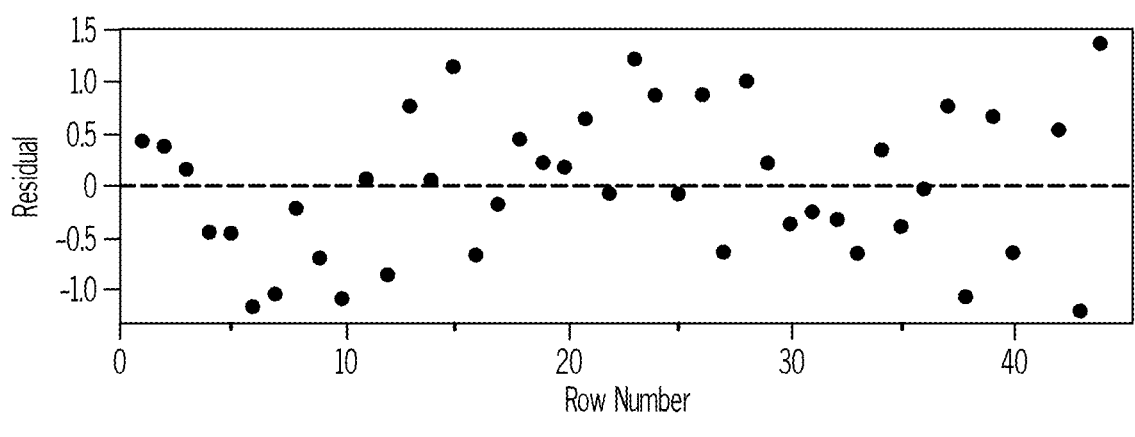
Figure 14E:
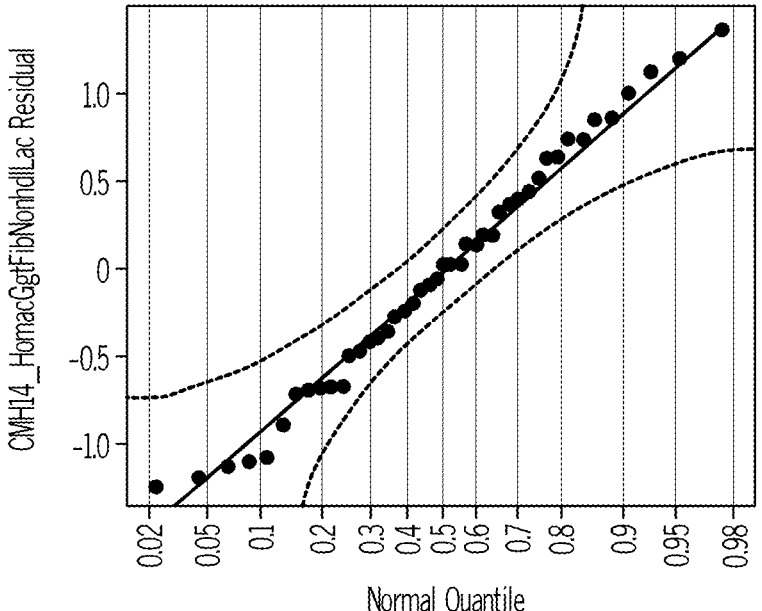
Figure 14F:
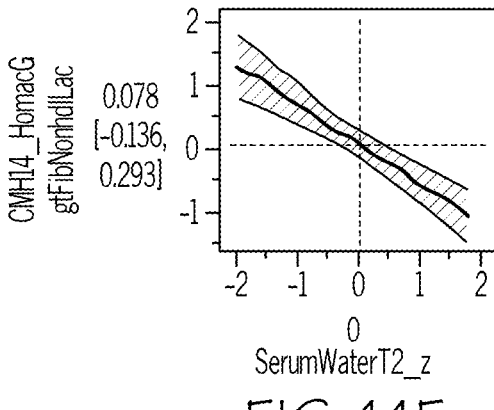
Figure 15A:
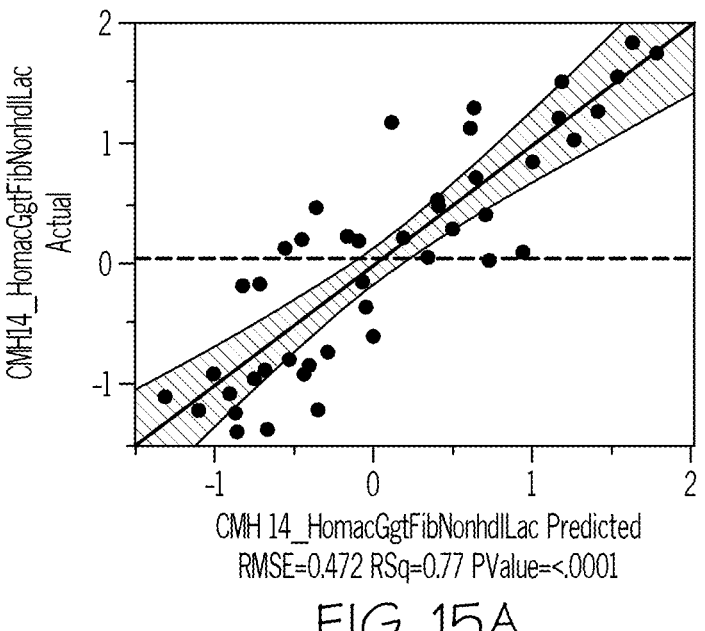
FIGS. 15A-15F provide multi-variable linear regression statistical reports for MR4B, including an actual by predicted plot (FIG. 15A), a residual by predicted plot (FIG. 15B), a studentized residuals plot (FIG. 15C), a residual by row plot (FIG. 15D), a residual normal quantile plot (FIG. 15E), and a prediction profiler (FIG. 15F).
Figure 15B:
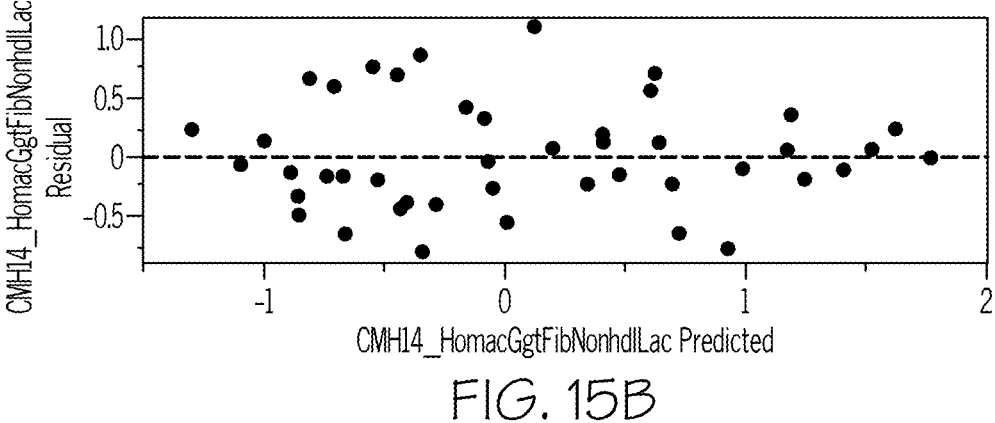
Figure 15C:
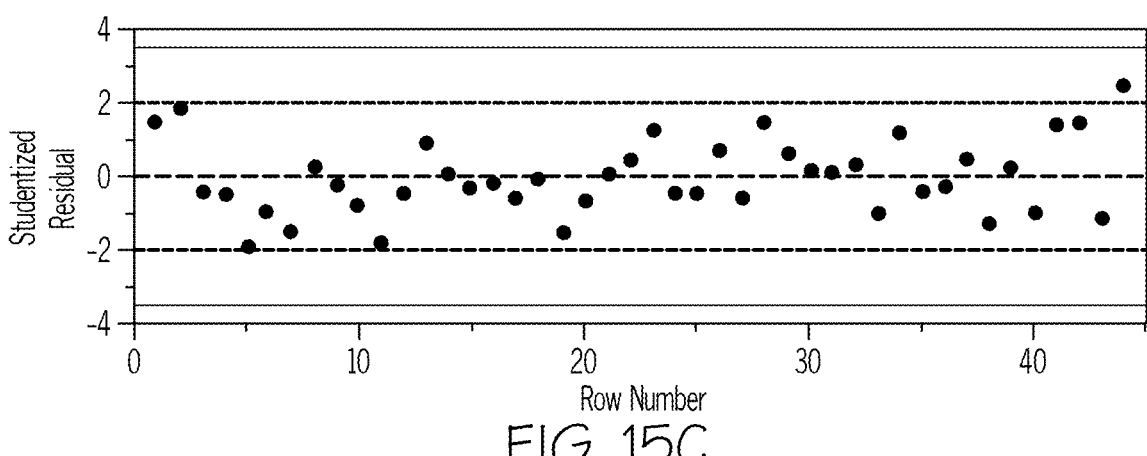
Figures 15D, 15E:
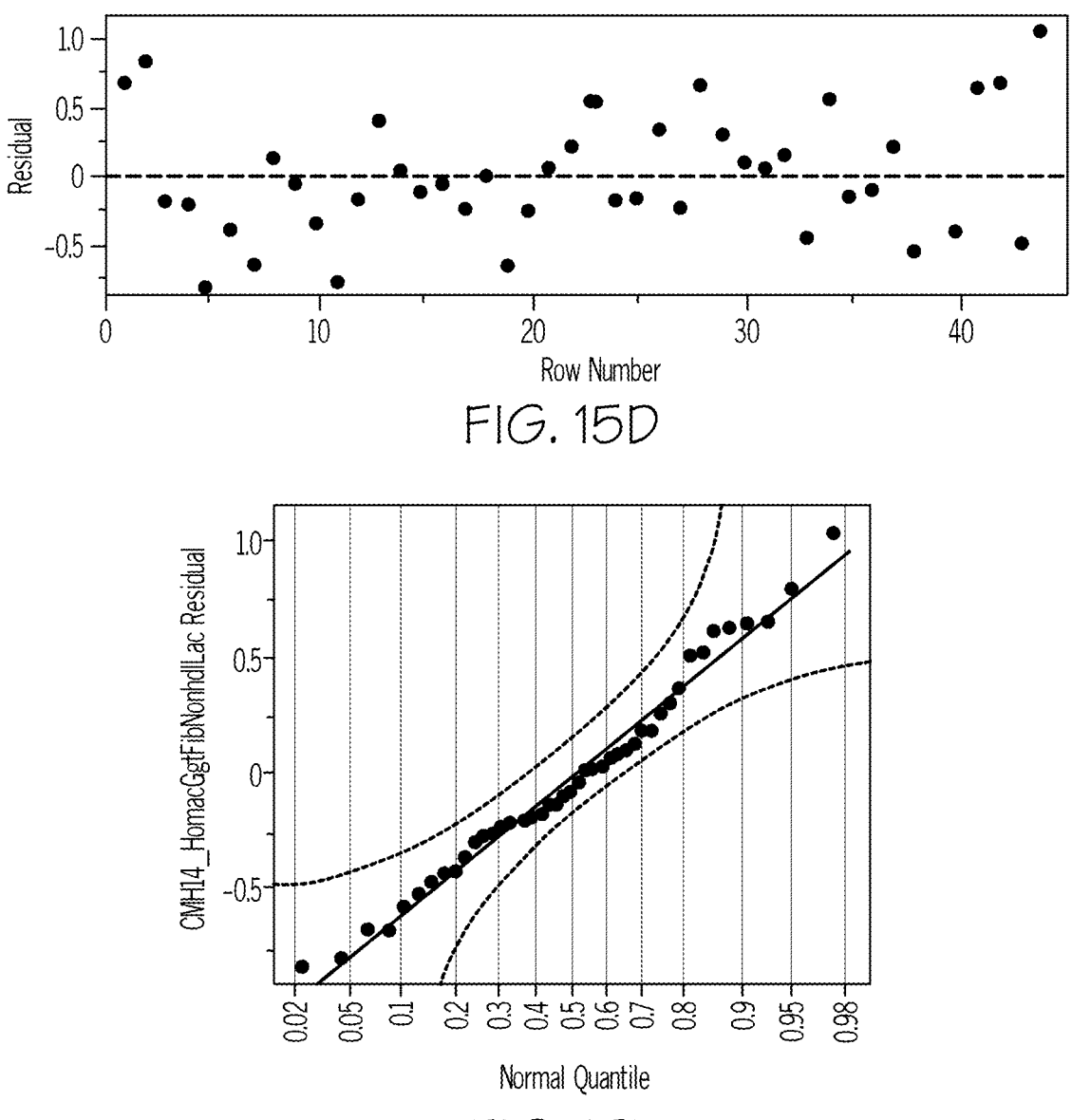
Figure 15F:
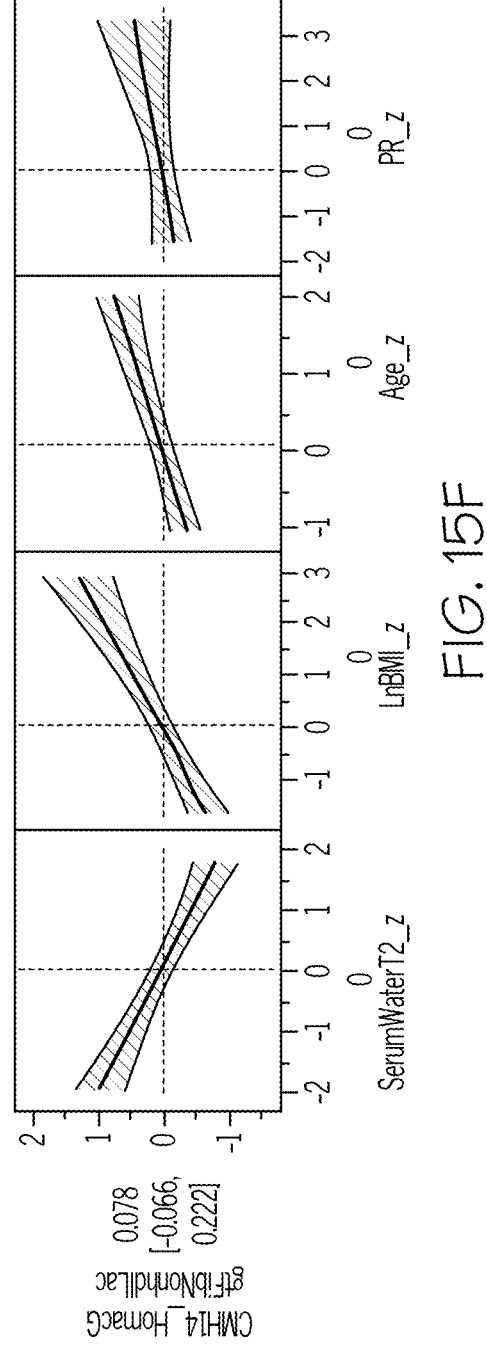
Figure 16A:
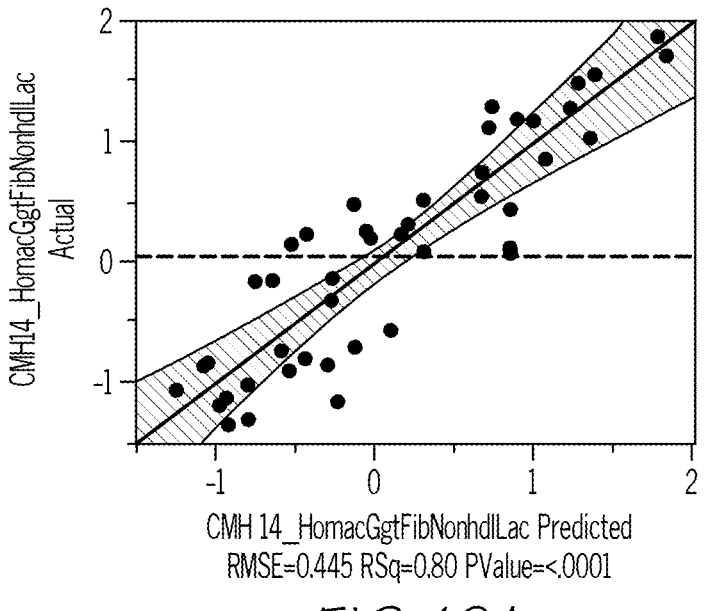
FIGS. 16A-16F provide multi-variable linear regression statistical reports for MR4C, including an actual by predicted plot (FIG. 16A), a residual by predicted plot (FIG. 16B), a studentized residuals plot (FIG. 16C), a residual by row plot (FIG. 16D), a residual normal quantile plot (FIG. 16E), and a prediction profiler (FIG. 16F).
Figure 16B:
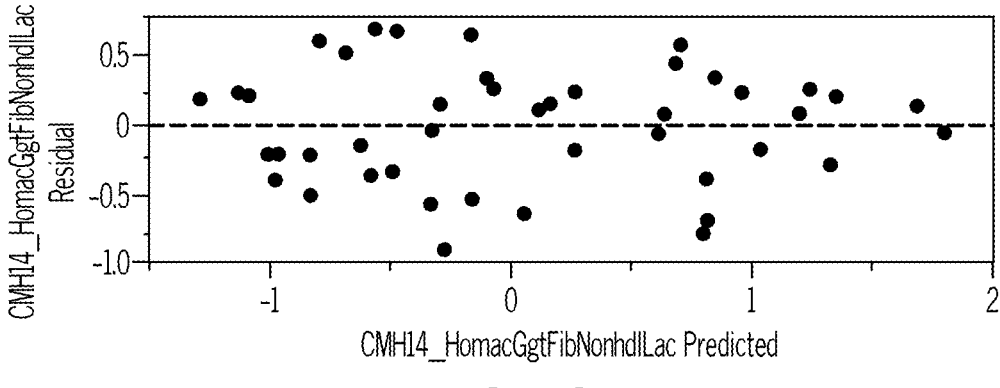
Figure 16C:
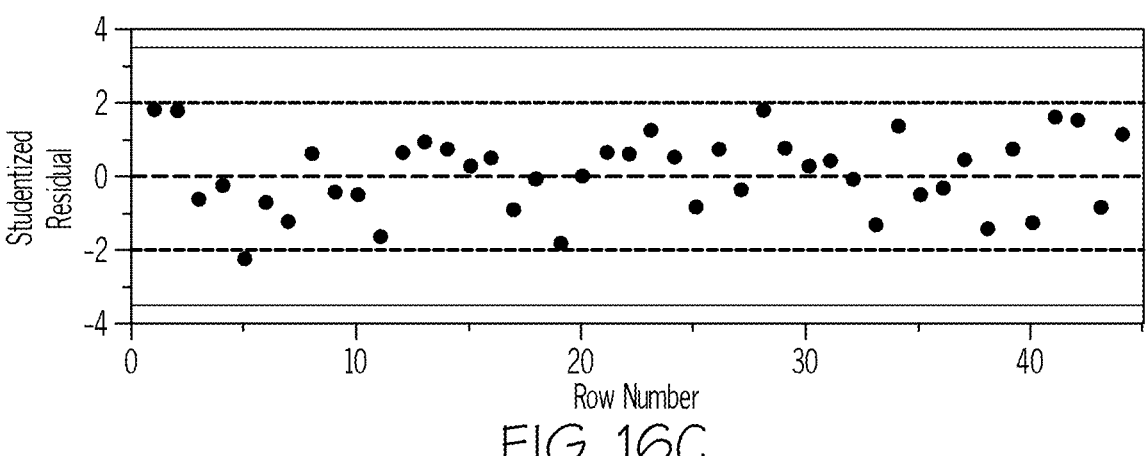
Figures 16D, 16E:
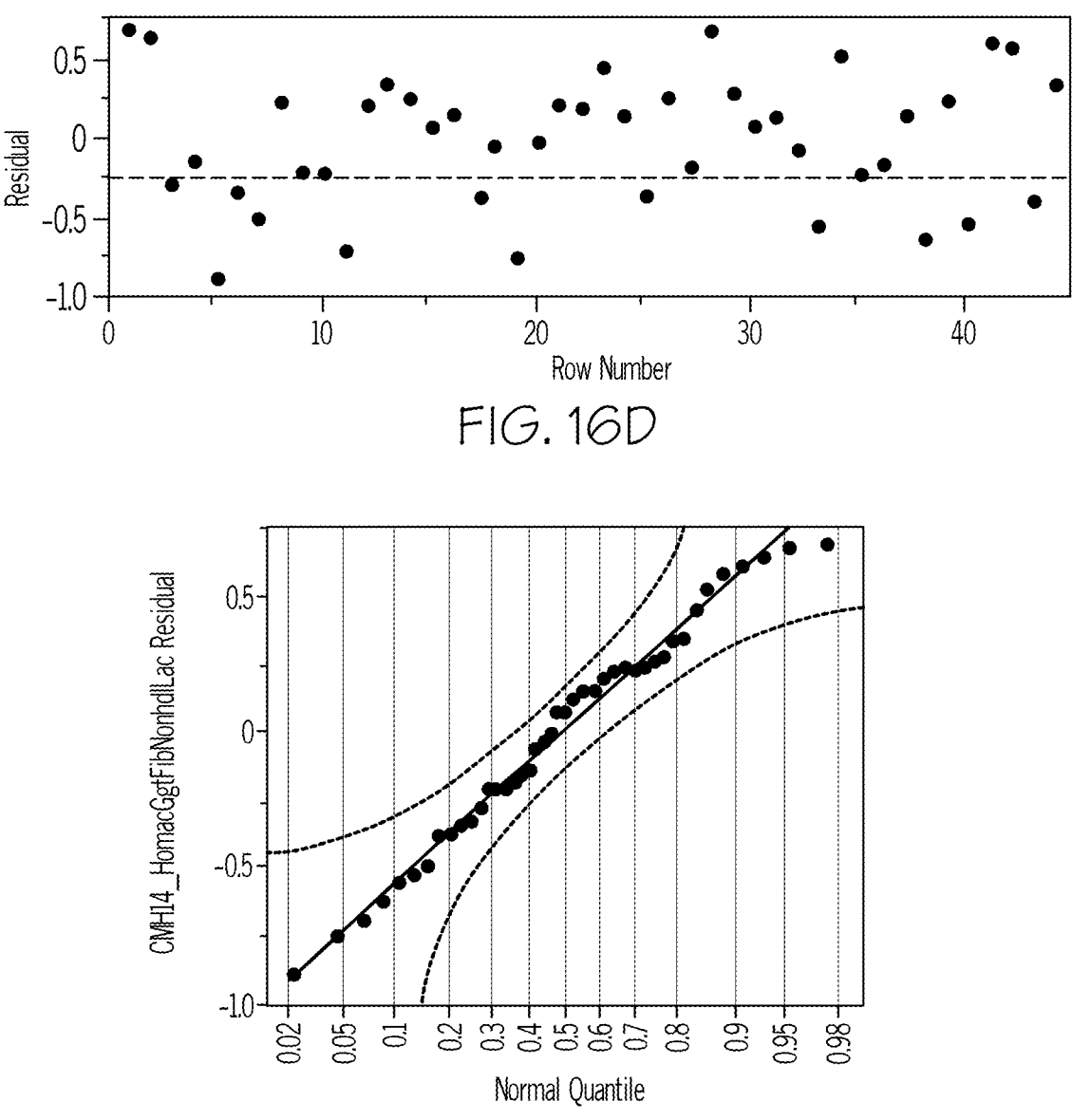
Figure 16F:
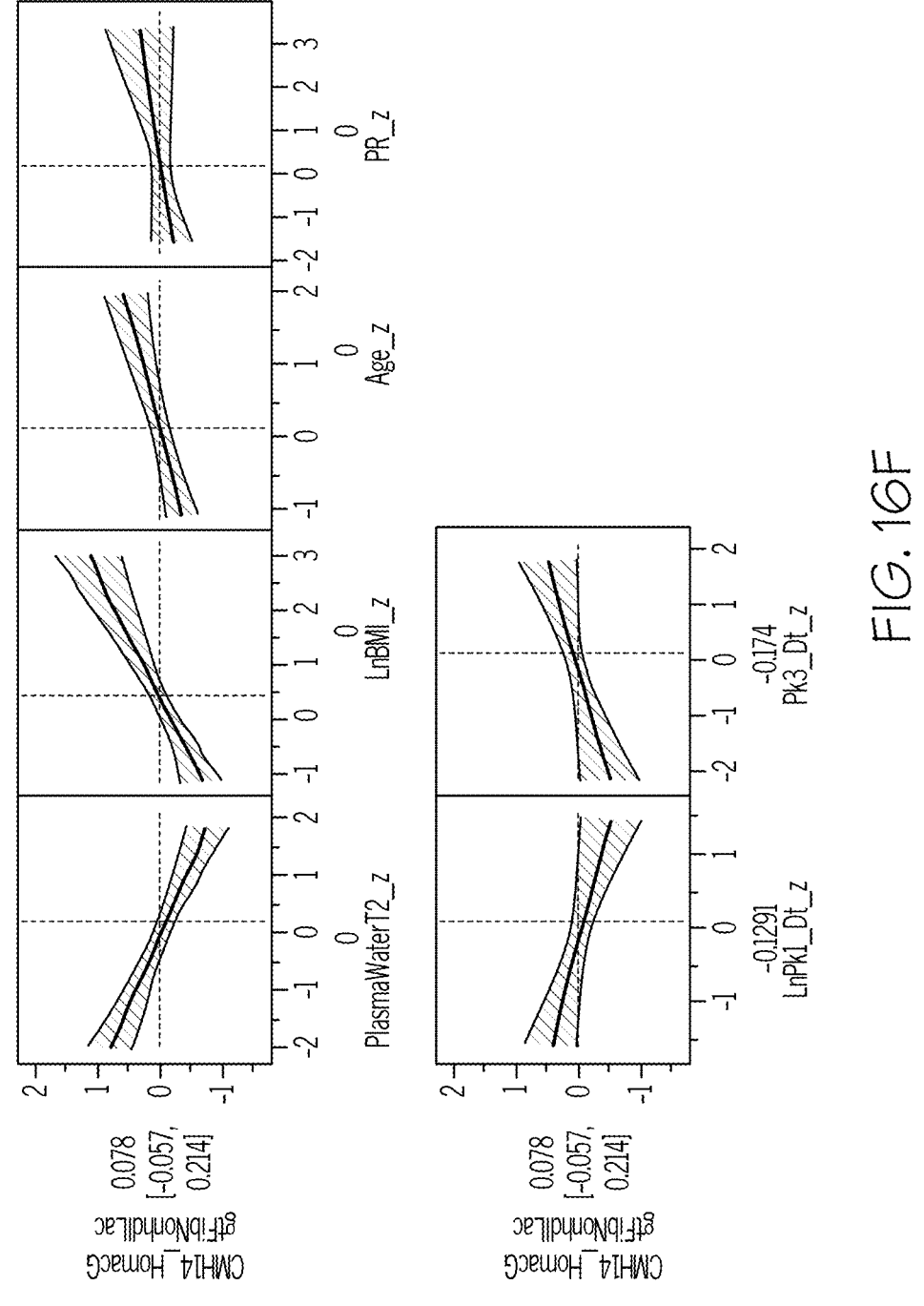
Figure 17A:
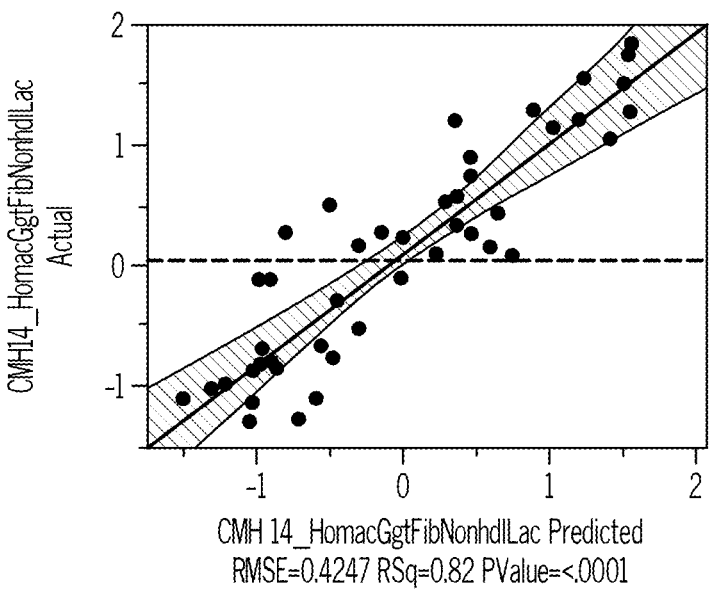
FIGS. 17A-17F provide multi-variable linear regression statistical reports for MR4D, including an actual by predicted plot (FIG. 17A), a residual by predicted plot (FIG. 17B), a studentized residuals plot (FIG. 17C), a residual by row plot (FIG. 17D), a residual normal quantile plot (FIG. 17E), and a prediction profiler (FIG. 17F).
Figure 17B:
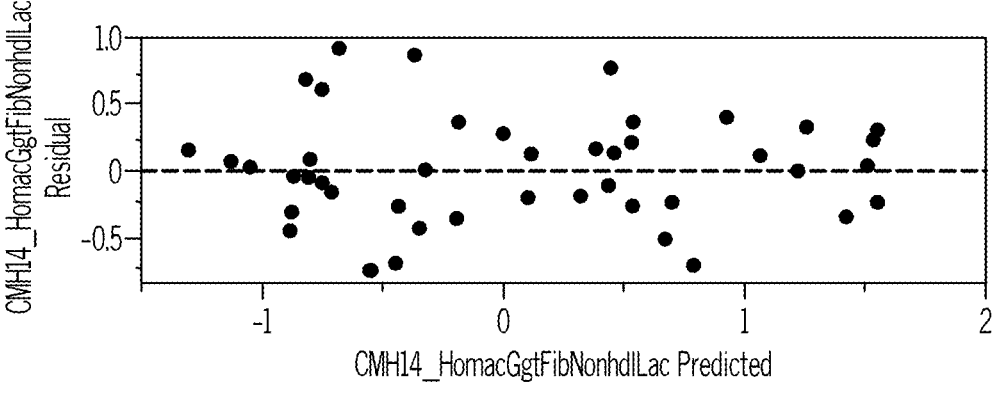
Figure 17C:
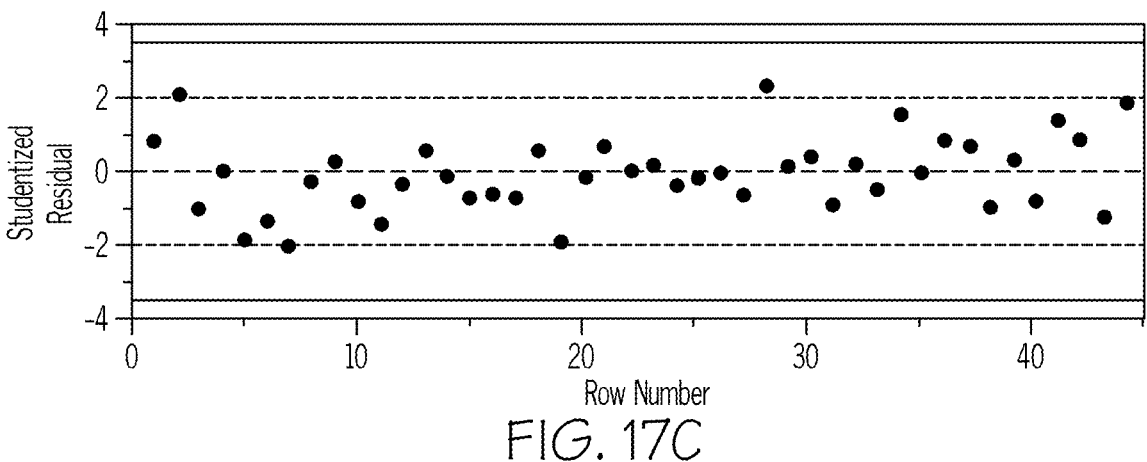
Figures 17D, 17E:
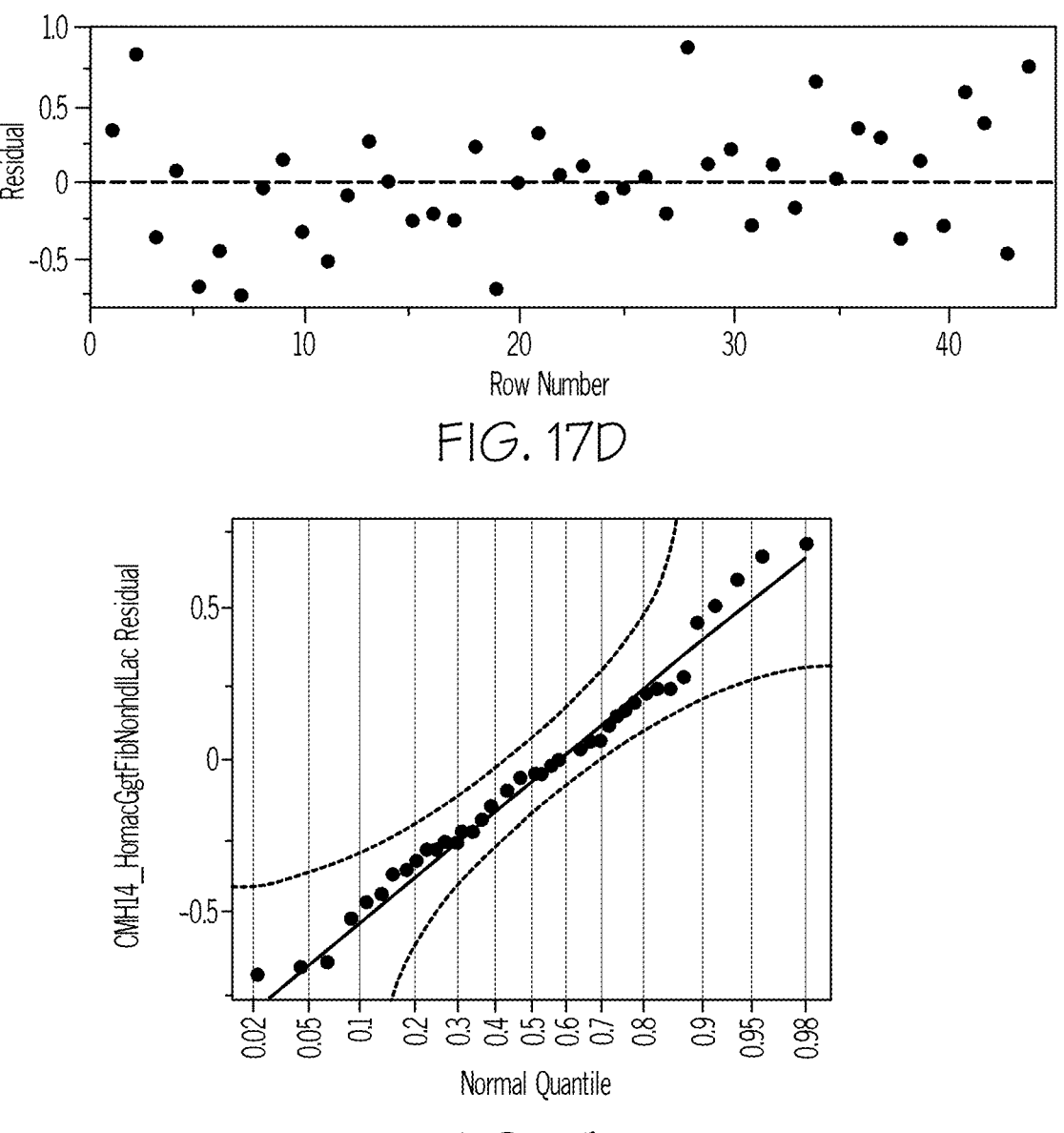
Figure 17F:
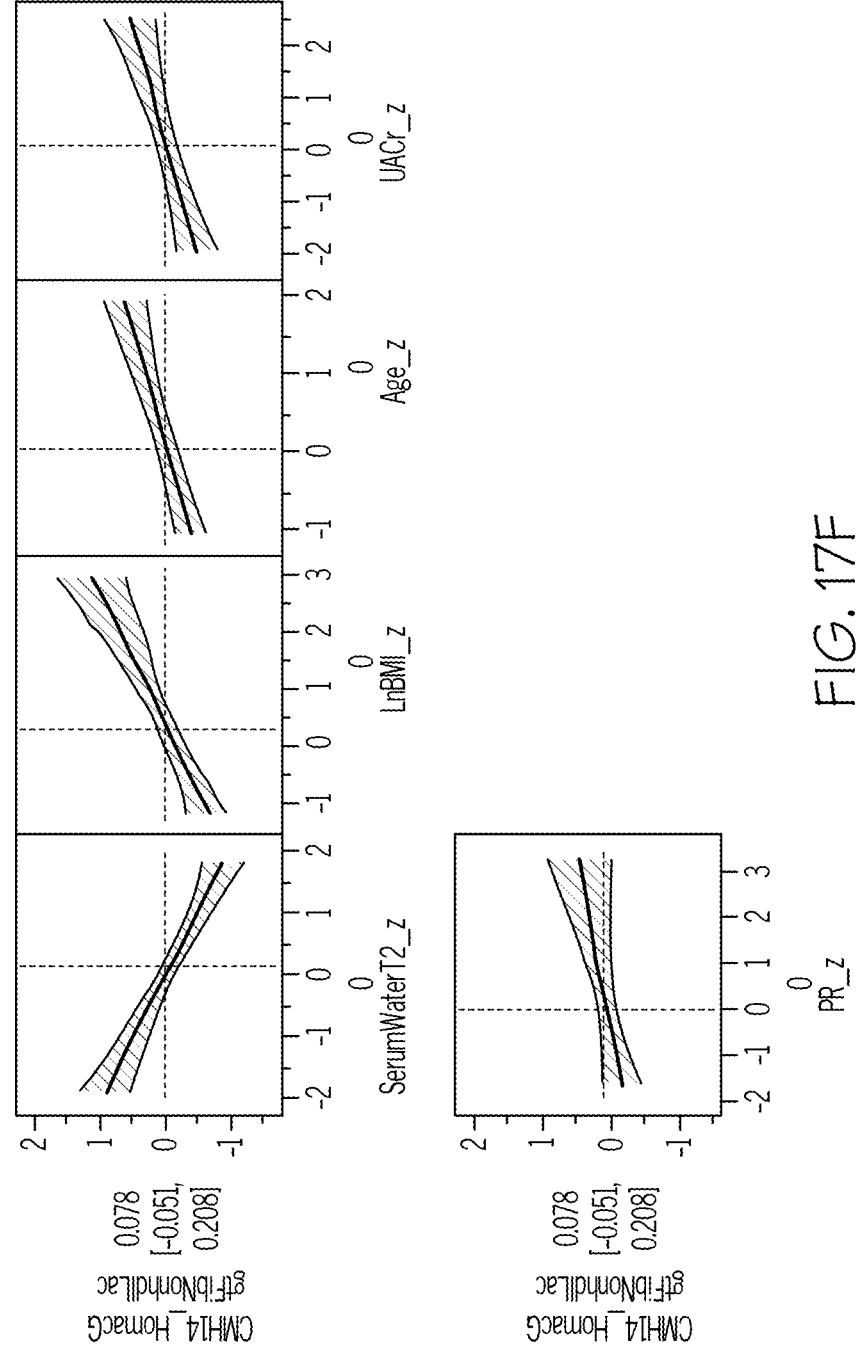

Embodiments of the present disclosure for assessing cardiometabolic health as discussed herein may be implemented using a system illustrated in FIG. 1B. Referring now to FIG. 1B, FIG. 1B illustrates an embodiment of the present disclosure of the hardware configuration of a system 30 which is representative of a hardware environment for practicing various embodiments of the present disclosure.

System 30 has a processor 31 connected to various other components by system bus 32. An operating system 33 runs on processor 31 and provides control and coordinates the functions of the various components of FIG. 1B. An application 34 in accordance with the principles of the present disclosure runs in conjunction with operating system 33 and provides calls to operating system 33, where the calls implement the various functions or services to be performed by application 34. Application 34 may include, for example, a program for assessing cardiometabolic health as discussed in the present disclosure, such as in connection with FIGS. 1A and 2A-17F.

Referring again to FIG. 1B, read-only memory ("ROM") 35 is connected to system bus 32 and includes a basic input/output system ("BIOS") that controls certain basic functions of system 30. Random access memory ("RAM") 36 and disk adapter 37 are also connected to system bus 32. It should be noted that software components including operating system 33 and application 34 may be loaded into RAM 36, which may be system's 30 main memory for execution. Disk adapter 37 may be an integrated drive electronics ("IDE") adapter that communicates with a disk unit 38 (e.g., a disk drive). It is noted that the program for assessing cardiometabolic health, as discussed in the present disclosure, such as in connection with FIGS. 1A and 2A-17F may reside in disk unit 38 or in application 34.

System 30 may further include a communications adapter 39 connected to system bus 32. Communications adapter 39 interconnects system bus 32 with an outside network (e.g., wide area network) to communicate with other devices.

Aspects of the present invention are described herein with reference to flowchart illustrations and/or block diagrams of methods, apparatus (systems), and systems according to embodiments of the invention. It will be understood that each block of the flowchart illustrations and/or block diagrams and combinations of blocks in the flowchart illustrations and/or block diagrams can be implemented by computer-readable program instructions.

These computer-readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/ or other devices to function in a particular manner, such that the computer-readable storage medium having instructions stored therein includes an article of manufacture including instructions which implement aspects of the function/act specified in the flowchart and/or block diagram block or blocks. The computer-readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and systems according to various embodiments of the present disclosure. In this regard, each block in the flowchart or block diagrams may represent a module, segment, or portion of instructions, which includes one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Applications and Advantages

The methods and systems of the present disclosure provide numerous advantages. For instance, in some embodiments, the methods and systems of the present disclosure can be used to detect hidden and asymptomatic conditions not detected by conventional medical exams, diagnostic tests, and screening tests. In some embodiments, the methods and systems of the present disclosure address an urgent need for a broad-based screening test as opposed to a large panel of narrowly focused diagnostic tests not designed for screening. In some embodiments, the methods and systems of the present disclosure provide simplified models for risk communication and management.

As such, the methods and systems of the present disclosure can provide numerous applications. For instance, in some embodiments, the methods and systems of the present disclosure provide practical, cost-effective and efficient approaches for health promotion, performance improvement, and disease prevention. In some embodiments, the methods and systems of the present disclosure can be utilized in various markets, such as markets related to wellness, fitness, and medical diagnostics.

ADDITIONAL EMBODIMENTS

Reference will now be made to more specific embodiments of the present disclosure and experimental results that provide support for such embodiments. However, Applicant notes that the disclosure below is for illustrative purposes only and is not intended to limit the scope of the claimed subject matter in any way.

Example 1. Methods and Tools for Predicting Cardiometabolic Health by Combining Blood $T_2$ Parameters with Other Measures Previously, Applicant reported that plasma or serum water $T_2$ can be used effectively to diagnose insulin resistance and assess health status. Those reports established how plasma or serum water $T_2$ could be used on its own for that purpose.

In this Example, Applicant describes new methods that combine plasma or serum water $T_2$ with: 1) readily available measures, such as body-mass index, age and/or self-reported lifestyle measures; 2) specific clinical lab tests such as uric acid or uric acid/creatinine ratio; or 3) emerging new biomarkers such as dynamic light scattering or whole blood $T_2$ measures ($T_{2P}$ and $T_{2S}$). These new methods that combine plasma or serum water $T_2$ with other measures are based on rigorous statistical analysis of linear regression models. The models unveiled a substantial increase in the predictive power of plasma and serum water $T_2$ for cardiometabolic health when combined with other measures.

Properly calibrated regression models can be used to estimate a "$T_2$ Health Index", whereby an individual's health status can be estimated from a plasma or serum $T_2$ value along with other relevant information. Plasma and serum water $T_2$, especially when combined with other simple measures, has a high predictive power for assessing early metabolic imbalance and assessing cardiometabolic health.

In spite of over a decade of discovery research on blood $T_2$ measurements, the quantitative impact and value of combining plasma or serum water $T_2$ with other information was unveiled to Applicant only during extensive statistical analysis. Applicant has established proof of concept, as only data from Phase 2 (n=44). Phase 2 included additional health measures not recorded during Phase 1, such as pulse rate (PR), lactate, fibrinogen and uric acid/creatinine ratio. Statistical analysis was performed using JMP Pro v17.2.

Table 1 shows measures of predictive accuracy derived from multi-variable linear regression (non-limiting examples).

TABLE 1

Measures of predictive accuracy derived from multi-variable linear regression.

| Regression Model # | Predictor Variables (X) | Measures of Predictive Accuracy: | | | | |
|---|---|---|---|---|---|---|
| | | $R^2$adj | RMS Error | AICc | BIC | Model p-value |
| Phase 1 & 2 (N = 72), Y = CMH1 | | | | | | |
| MR1A | Plasma water T2 | 0.454 | 0.659 | 148.6 | 155.1 | <0.0001 |
| MR1B | Plasma T2, BMI, Age | 0.689 | 0.486 | 107.3 | 117.7 | <0.0001 |
| MR1C | Plasma T2, BMI, Age, DLS-Pks1+3-Dt | 0.706 | 0.484 | 109.2 | 123.4 | <0.0001 |
| MR2A | Serum water T2 | 0.261 | 0.767 | 170.4 | 176.9 | <0.0001 |
| MR2B | Serum T2, LnBMI, Age40+ | 0.604 | 0.562 | 128.1 | 138.5 | <0.0001 |
| MR2C | Serum T2, LnBMI, Age, DLS_Pks1+3_Dt | 0.693 | 0.495 | 111.0 | 123.4 | <0.0001 |
| Phase 2 only (N = 44), Y = CMH14 | | | | | | |
| MR3A | Plasma water T2 | 0.631 | 0.566 | 79.3 | 84.0 | <0.0001 |
| MR3B | Plasma T2, BMI, Age, Pulse Rate (PR) | 0.796 | 0.421 | 57.7 | 66.1 | <0.0001 |
| MR3C | Plasma T2, BMI, Age, PR, DLS_Pk1_Dt | 0.813 | 0.402 | 55.4 | 64.8 | <0.0001 |
| MR3D | Plasma T2, BMI, Age, PR, UACr | 0.840 | 0.372 | 48.5 | 48.5 | <0.0001 |
| MR4A | Serum water T2 | 0.429 | 0.704 | 98.5 | 103.3 | <0.0001 |
| MR4B | Serum T2, BMI, Age, PR | 0.743 | 0.472 | 67.8 | 76.2 | <0.0001 |
| MR4C | Serum T2, BMI, Age, PR, DLS_Pks1+3_Dt | 0.772 | 0.445 | 66.0 | 76.2 | <0.0001 |
| MR4D | Serum T2, BMI, Age, PR, UACr | 0.792 | 0.425 | 60.2 | 69.5 | <0.0001 |

Abbreviations:
CMH1 and CMH14, latent variables for cardiometabolic health defined below;
T2, transverse relaxation time constant from magnetic resonance;
BMI, body-mass index;
Pk, peak;
DLS, dynamic light scattering;
Dt, diffusion time from DLS;
UACr, serum uric acid/creatinine ratio;
RMS, root mean square;
R2adj, adjusted regression coefficient squared;
AICc, Akaike information criterion;
BIC, Bayesian information criterion.

shown in this Example. In addition, Applicant has reduced the concept to practice by generating a series of regression models that can be used to predict the cardiometabolic health status of an individual, given the input data (e.g., $T_2$ combined with BMI, age or other information).

In particular, multi-variable linear regression (MR) analyses were used to quantify the power of plasma and serum water $T_2$ for predicting cardiometabolic health when combined with other measures. The combinations included the following: (1) Plasma or serum $T_2$ plus readily available measures such as age, body-mass index and pulse rate; (2) $T_2$ plus available measures plus other blood tests such as uric acid/creatinine ratio; and (3) $T_2$ plus available measures plus dynamic light scattering diffusion times and/or intensities.

These analyses were performed using data from 72 asymptomatic individuals with no active acute or chronic disease but spanning a range of cardiometabolic health. Each individual was phenotyped using over 100 health markers and medical laboratory tests. The markers included measurements of plasma and serum water $T_2$ derived from benchtop magnetic resonance relaxometry, and diffusion times (Dt) derived from dynamic light scattering (DLS). Some regression models utilized data from both Phase 1 and Phase 2 of the study (n=72), whereas other models utilized In each MR model, the outcome or Y-variable was a multiplex measure of cardiometabolic health. The latent variable CMH1 incorporated measures of insulin resistance (HOMA-IR), glucose tolerance (hemoglobin A1c), dyslipidemia (non-HDL-cholesterol), and cell damage/oxidative stress (GGT) into one combined variable. The latent variable CMH14 incorporated measures of insulin resistance (HOMA-IR), inflammation/pro-coagulation (fibrinogen), hypoxia (lactate), dyslipidemia (non-HDL-cholesterol), and cell damage/oxidative stress (gamma glutamyl transferase or GGT). The higher the value, the worse the cardiometabolic health. Full statistical reports describing the generation of CMH1 and CMH14 are provided in FIGS. 2A-3B. A full statistical report for each MR model from Table 1 is provided in FIGS. 4A-17F.

The most important measure of predictive accuracy or power is the adjusted R-squared ($R^2$adj) value, the $5^{th}$ column from the right in Table 1. A perfectly predictive model with no uncertainty or error has a $R^2$adj=1.0. The value is interpreted as the fraction or percent of variance in the Y-variable (outcome variable) predicted by variance in the predictor X-variables. For example, in model MR3C (FIGS. 12A-12F), the variance in the predictor variables explains 81.3% of the variance in cardiometabolic health (CMH14, FIGS. 3A-3B). This indicates a remarkably high predictive power.

The predictive power of plasma water $T_2$ by itself is 45.4% and 63.1% (MR1A and MR3A, respectively, as set forth in FIGS. 4A-4F and 10A-10F, respectively). Based on the magnitude of its standardized beta coefficient in each model, plasma $T_2$ is the strongest individual predictor of cardiometabolic health. However, with the addition of readily available measures such as BMI, age and pulse rate, the predictive power of the plasma water $T_2$ model increases dramatically: from 45.4 to 68.9% and from 63.1 to 79.6% (MR1A (FIGS. 4A-4F) v. MR1B (FIGS. 5A-5F) and MR3A (FIGS. 10A-10F) v. MR3B (FIGS. 11A-11F), respectively). The best model with plasma water $T_2$ has a predictive power of 84.0% (MR3D, FIGS. 13A-13F). Models using serum rather than plasma water $T_2$ as a predictor variable show similar trends (Table 1).

These large increases in predictive power (accuracy) were significant, as health-related variables often overlap in the information they provide. That overlap would be evidenced by statistical confounding, which was not observed here. Rather, Applicant's novel regression results indicate that plasma and serum water $T_2$ provide predictive health information largely independent of that provided by BMI, age, resting pulse rate, DLS diffusion time or intensities, or uric acid/creatinine ratio.

Other important measures of predictive accuracy are provided in Table 1. Those include RMS error, AICc, and BIC. For each of these measures, the lower the value, the better the model fit. The numbers are interpreted in a relative manner. All regression models provide statistically significant fits to the data, evidenced by model p-values <0.0001.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of assessing the cardiometabolic health of a subject, said method comprising:

receiving a plurality of parameters of the subject, wherein the plurality of parameters comprises a combination of:

a $T_2$ relaxation time constant of the subject's blood ($T_2$ value), and one or more additional parameters, wherein the one or more additional parameters is selected from the group consisting of body-mass index, age, serum uric acid/creatinine ratio, resting pulse rate, dynamic light scattering diffusion times of the subject's blood, dynamic light scattering diffusion intensities of the subject's blood, or combinations thereof;

feeding the plurality of parameters into an algorithm, wherein the algorithm comprises a multi-variable regression algorithm that utilizes multi-variable regression (MR) analyses to correlate the received $T_2$ relaxation time and the one or more additional parameters to the subject's cardiometabolic health, wherein the correlation comprises a prediction of the subject's susceptibility to one or more cardiometabolic health-related conditions; and implementing a treatment decision based on the subject's predicted susceptibility to the one or more cardiometabolic health-related conditions, wherein the treatment decision comprises administering a therapeutic agent to the subject.

2. The method of claim 1, wherein the $T_2$ value represents the spin-spin relaxation time constant of the isolated plasma component of the blood sample (plasma water $T_2$).

3. The method of claim 1, wherein the $T_2$ value represents the spin-spin relaxation time constant of the isolated serum component of the blood sample (serum water $T_2$).

4. The method of claim 1, wherein the $T_2$ value represents the spin-spin relaxation time constant of the settled blood cell pellet component of an anti-coagulated whole blood sample ($T_{2P}$).

5. The method of claim 1, wherein the $T_2$ value represents the spin-spin relaxation time constant of the supernatant liquid component of an anti-coagulated whole blood sample ($T_{2S}$).

6. The method of claim 1, wherein the $T_2$ value represents the spin-spin relaxation time constant of a mixed and unsettled whole blood sample (whole blood $T_2$).

7. The method of claim 1, wherein the $T_2$ value is represented in the following formula:

$$I(t) = \sum_i A_i e^{-t/T_{2i}}$$

wherein I(t) represents the nuclear magnetic resonance (NMR) signal intensity, t represents time, $A_i$ represents the signal amplitude, and $T_{2i}$ represents the transverse relaxation time constant of ith proton microenvironment or mobility domain.

8. The method of claim 1, wherein the one or more additional parameters comprises: age, body-mass index, and pulse rate; uric acid/creatinine ratio; or dynamic light scattering diffusion times of the subject's blood, dynamic light scattering diffusion intensities of the subject's blood.

9. The method of claim 1, wherein the plurality of parameters comprise a $T_2$ value, age, body-mass index, and resting pulse rate.

10. The method of claim 1, wherein the plurality of parameters comprise a $T_2$ value and serum uric acid/creatinine ratio.

11. The method of claim 1, wherein the plurality of parameters comprise a $T_2$ value and at least one of dynamic light scattering diffusion intensities of the subject's blood and/or dynamic light scattering diffusion times of the subject's blood.

12. The method of claim 1, wherein the algorithm comprises a machine-learning algorithm, or an artificial intelligence algorithm trained on the plurality of parameters.

13. The method of claim 1, wherein the correlation further comprises a quantitative estimation of a subject's current cardiometabolic health status, diagnosis of a cardiometabolic health-related condition in the subject, or combinations thereof.

14. The method of claim 1, wherein the correlation comprises a prediction of the subject's current cardiometabolic health status and susceptibility to one or more future cardiometabolic health-related conditions.

15. The method of claim 1, wherein the one or more cardiometabolic health-related conditions is selected from the group consisting of metabolic syndrome, early metabolic syndrome, metabolic dysregulation, early metabolic dysregulation, metabolic imbalance, early metabolic imbalance, diabetes, prediabetes, type 2 diabetes, gestational diabetes, insulin resistance, dyslipidemia, oxidative stress, subclinical inflammation, hypoxemia, subclinical hypoxemia, hypoxia, subclinical hypoxia, cardiovascular disease, endocrine disorders, hormonal disorders, kidney dysfunction, kidney failure, metabolism-associated fatty liver disease (MAFLD), steatohepatitis (MASH), cognition decline, dementia, or combinations thereof.

16. The method of claim 1, further comprising a step of communicating cardiometabolic health risk.

17. The method of claim 1, wherein the treatment decision further comprises a personalized treatment plan for the subject based on the prediction of the subject's susceptibility to one or more cardiometabolic health-related conditions.

18. The method of claim 1, wherein the method is repeated after implementing the treatment decision.

19. The method of claim 1, wherein the subject is a human being.

20. The method of claim 1, wherein the subject shows no visible signs or symptoms related to cardiometabolic health-related conditions.

* * * * *